United States Patent
Yanagidate

(10) Patent No.: US 10,159,403 B2
(45) Date of Patent: Dec. 25, 2018

(54) CAPSULE ENDOSCOPE SYSTEM, CAPSULE ENDOSCOPE, RECEPTION APPARATUS, IMAGING CONTROL METHOD OF CAPSULE ENDOSCOPE, AND COMPUTER READABLE STORAGE DEVICE

(71) Applicant: OLYMPUS CORPORATION, Tokyo (JP)

(72) Inventor: Masaharu Yanagidate, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 645 days.

(21) Appl. No.: 14/688,552

(22) Filed: Apr. 16, 2015

(65) Prior Publication Data

US 2015/0297067 A1    Oct. 22, 2015

(30) Foreign Application Priority Data

Apr. 18, 2014 (JP) .................................. 2014-086241

(51) Int. Cl.
*A61B 1/04* (2006.01)
*A61B 1/00* (2006.01)
(Continued)

(52) U.S. Cl.
CPC .......... *A61B 1/041* (2013.01); *A61B 1/00009* (2013.01); *A61B 1/00016* (2013.01);
(Continued)

(58) Field of Classification Search
CPC ... A61B 1/00181; A61B 1/043; A61B 1/0638; A61B 1/0676; A61B 5/065; A61B 5/6861
(Continued)

(56) References Cited

U.S. PATENT DOCUMENTS 8,328,712 B2 * 12/2012 Nishiyama ......... A61B 1/00009
                                                     600/109
2003/0174208 A1 *  9/2003 Glukhovsky ...... A61B 1/00193
                                                     348/131
(Continued)

FOREIGN PATENT DOCUMENTS

JP      2004-521662 A      7/2004
JP      2005-185544 A      7/2005
(Continued)

OTHER PUBLICATIONS

Notice of Allowance Japanese Patent Application No. 2014-086241 dated Nov. 7, 2017 with English translation.

*Primary Examiner* — Timothy J Neal
*Assistant Examiner* — Jae Woo
(74) *Attorney, Agent, or Firm* — Pillsbury Winthrop Shaw Pittman, LLP

(57) ABSTRACT

A capsule endoscope system includes: a capsule endoscope having a first imaging module configured to direct an imaging direction in a first direction, image a first imaging range, and output first image data, a second imaging module configured to direct an imaging direction in a second direction different from the first direction, image a second imaging range that does not overlap the first imaging range, and output second image data, and a first wireless communication interface configured to transmit the first image data and the second image data; and a reception apparatus having a second wireless communication interface configured to receive the first image data and the second image data. The capsule endoscope or the reception apparatus has a moving direction detecting section, a moving speed detecting section, a speed determining section, and an imaging instruction section.

8 Claims, 16 Drawing Sheets

(51) Int. Cl.
*A61B 1/045* (2006.01)
*A61B 5/06* (2006.01)
*A61B 5/00* (2006.01)

(52) U.S. Cl.
CPC .......... *A61B 1/00181* (2013.01); *A61B 1/045* (2013.01); *A61B 5/0084* (2013.01); *A61B 5/06* (2013.01); *A61B 5/067* (2013.01)

(58) Field of Classification Search
USPC ................................ 600/109, 103, 117, 118
See application file for complete search history.

(56) References Cited

U.S. PATENT DOCUMENTS

| | | | | |
|---|---|---|---|---|
| 2005/0143649 | A1* | 6/2005 | Minai | A61B 1/041 600/410 |
| 2006/0106318 | A1* | 5/2006 | Davidson | A61B 1/04 600/476 |
| 2007/0165932 | A1* | 7/2007 | Nishimura | A61B 1/00016 382/128 |
| 2007/0260139 | A1* | 11/2007 | Minai | A61B 1/00036 600/420 |
| 2008/0039692 | A1* | 2/2008 | Hirakawa | A61B 1/00045 600/160 |
| 2008/0242926 | A1* | 10/2008 | Nishino | A61B 1/04 600/109 |
| 2008/0312504 | A1* | 12/2008 | Kimoto | A61B 1/00016 600/118 |
| 2009/0196476 | A1* | 8/2009 | Inoue | A61B 1/04 382/128 |
| 2011/0275893 | A1* | 11/2011 | Kawano | A61B 1/00032 600/109 |
| 2013/0035547 | A1* | 2/2013 | Jung | A61B 1/00036 600/109 |
| 2015/0297067 | A1* | 10/2015 | Yanagidate | A61B 1/041 600/109 |
| 2017/0105610 | A1* | 4/2017 | On | A61B 1/041 |
| 2017/0231470 | A1* | 8/2017 | Yanagidate | A61B 1/00016 600/118 |
| 2017/0245736 | A1* | 8/2017 | Mitsuhashi | A61B 1/00009 |

FOREIGN PATENT DOCUMENTS

| | | |
|---|---|---|
| JP | 2006-068534 | 3/2006 |
| JP | 2007-236700 A | 9/2007 |
| JP | 2008-237640 A | 10/2008 |
| JP | 2009-195343 A | 9/2009 |
| JP | 2010-035746 A | 2/2010 |
| JP | 4864534 | 2/2012 |
| JP | 2012-228346 A | 11/2012 |
| JP | 2013-524928 A | 6/2013 |
| WO | 01/87377 A2 | 11/2001 |

\* cited by examiner

CAPSULE ENDOSCOPE SYSTEM, CAPSULE ENDOSCOPE, RECEPTION APPARATUS, IMAGING CONTROL METHOD OF CAPSULE ENDOSCOPE, AND COMPUTER READABLE STORAGE DEVICE

BACKGROUND OF THE INVENTION

Field of the Invention

The present invention relates to technology of a capsule endoscope having a plurality of imaging modules.

Priority is claimed on Japanese Patent Application No. 2014-086241, filed. Apr. 18, 2014, the entire content of which is hereby incorporated by reference.

Description of the Related Art

The diagnosis of a lesion part or the like is performed using an image captured by a capsule endoscope inserted into a living body. In the publication of Japanese Unexamined Patent Application, First Publication No. 2006-68534, a method of performing imaging by alternately driving a plurality of imaging sections in a capsule endoscope having the imaging sections is disclosed. In addition, in the publication of Japanese Patent No. 4864534, a method of detecting a speed of a capsule endoscope from an image captured by the capsule endoscope and preventing discontinuity in imaging by increasing a frame rate of the imaging when the capsule endoscope moves at a high speed is disclosed.

SUMMARY

According to a first aspect of the present invention, a capsule endoscope system includes: a capsule endoscope having a first imaging module configured to direct an imaging direction in a first direction, image a first imaging range, and output first image data, a second imaging module configured to direct an imaging direction in a second direction different from the first direction, image a second imaging range that does not overlap the first imaging range, and output second image data, and a first wireless communication interface configured to transmit the first image data and the second image data; and a reception apparatus having a second wireless communication interface configured to receive the first image data and the second image data, wherein the capsule endoscope or the reception apparatus has a moving direction detecting section configured to detect a moving direction of the capsule endoscope, a moving speed detecting section configured to detect a moving speed of the capsule endoscope, a speed determining section configured to determine whether the moving speed is greater than or equal to a predetermined speed, and an imaging instruction section configured to instruct an imaging module having an imaging direction closer to a moving direction between the first and second imaging modules to perform imaging at a first time interval and instruct an imaging module having an imaging direction farther from the moving direction to stop imaging or perform imaging at a second time interval which is the same as or different from the first time interval when the moving speed is less than the predetermined speed, and perform additional imaging if the imaging is stopped and perform additional imaging at a third time interval shorter than the second time interval if the imaging at the second time interval is in execution when the moving speed is greater than or equal to the predetermined speed.

According to a second aspect of the present invention, a capsule endoscope includes: a first imaging module configured to direct an imaging direction in a first direction, image a first imaging range, and output first image data; a second imaging module configured to direct an imaging direction in a second direction different from the first direction, image a second imaging range that does not overlap the first imaging range, and output second image data; a wireless communication interface configured to transmit the first image data and the second image data; a moving direction detecting section configured to detect a moving direction of the capsule endoscope; a moving speed detecting section configured to detect a moving speed of the capsule endoscope; a speed determining section configured to determine whether the moving speed is greater than or equal to a predetermined speed; and an imaging instruction section configured to instruct an imaging module having an imaging direction closer to a moving direction between the first and second imaging modules to perform imaging at a first time interval and instruct an imaging module having an imaging direction farther from the moving direction to stop imaging or perform imaging at a second time interval which is the same as or different from the first time interval when the moving speed is less than the predetermined speed and perform additional imaging if the imaging is stopped and perform additional imaging at a third time interval shorter than the second time interval if the imaging at the second time interval is in execution when the moving speed is greater than or equal to the predetermined speed.

According to a third aspect of the present invention, a reception apparatus includes: a second wireless communication interface configured to receive first image data and second image data from a capsule endoscope having a first imaging module configured to direct an imaging direction in a first direction, image a first imaging range, and output the first image data; a second imaging module configured to direct an imaging direction in a second direction different from the first direction, image a second imaging range that does not overlap the first imaging range, and output the second image data; and a first wireless communication interface configured to transmit the first image data and the second image data; a moving direction detecting section configured to detect a moving direction of the capsule endoscope; a moving speed detecting section configured to detect a moving speed of the capsule endoscope; a speed determining section configured to determine whether the moving speed is greater than or equal to a predetermined speed; and an imaging instruction section configured to transmit instruction data for instructing an imaging module having an imaging direction closer to a moving direction between the first and second imaging modules to perform imaging at a first time interval and instructing an imaging module having an imaging direction farther from the moving direction to stop imaging or perform imaging at a second time interval which is the same as or different from the first time interval when the moving speed is less than the predetermined speed and perform additional imaging if the imaging is stopped and perform additional imaging at a third time interval shorter than the second time interval if the imaging at the second time interval is in execution when the moving speed is greater than or equal to the predetermined speed from the second wireless communication interface to the capsule endoscope.

According to a fourth aspect of the present invention, an imaging control method of a capsule endoscope, comprising the steps of: determining whether a moving speed of the capsule endoscope is greater than or equal to a predetermined speed, wherein the capsule endoscope has a first imaging module configured to direct an imaging direction in a first direction, image a first imaging range, and output first image data; a second imaging module configured to direct an imaging direction in a second direction different from the first direction, image a second imaging range that does not overlap the first imaging range, and output second image data; and a wireless communication interface configured to transmit the first image data and the second image data; and instructing an imaging module having an imaging direction closer to a moving direction between the first and second imaging modules to perform imaging at a first time interval and instructing an imaging module having an imaging direction farther from the moving direction to stop imaging or perform imaging at a second time interval which is the same as or different from the first time interval when the moving speed is less than the predetermined speed and perform additional imaging if the imaging is stopped and perform additional imaging at a third time interval shorter than the second time interval if the imaging at the second time interval is in execution when the moving speed is greater than or equal to the predetermined speed.

According to a fifth aspect of the present invention, a computer readable storage device saving a computer program for causing a computer of a capsule endoscope to execute the steps of: determining whether a moving speed of the capsule endoscope is greater than or equal to a predetermined speed, wherein the capsule endoscope has a first imaging module configured to direct an imaging direction in a first direction, image a first imaging range, and output first image data; a second imaging module configured to direct an imaging direction in a second direction different from the first direction, image a second imaging range that does not overlap the first imaging range, and output second image data; and a wireless communication interface configured to transmit the first image data and the second image data; and instructing an imaging module having an imaging direction closer to a moving direction between the first and second imaging modules to perform imaging at a first time interval and instructing an imaging module having an imaging direction farther from the moving direction to stop imaging or perform imaging at a second time interval which is the same as or different from the first time interval when the moving speed is less than the predetermined speed and perform additional imaging if the imaging is stopped and perform additional imaging at a third time interval shorter than the second time interval if the imaging at the second time interval is in execution when the moving speed is greater than or equal to the predetermined speed.

According to a sixth aspect of the present invention, a computer readable storage device saving a computer program for causing a computer of a reception apparatus having a second wireless communication interface to execute the steps of: determining whether a moving speed of the capsule endoscope is greater than or equal to a predetermined speed, wherein the capsule endoscope has a first imaging module configured to direct an imaging direction in a first direction, image a first imaging range, and output first image data; a second imaging module configured to direct an imaging direction in a second direction different from the first direction, image a second imaging range that does not overlap the first imaging range, and output second image data; and a wireless communication interface configured to transmit the first image data and the second image data; and transmitting instruction data for instructing an imaging module having an imaging direction closer to a moving direction between the first and second imaging modules to perform imaging at a first time interval and instructing an imaging module having an imaging direction farther from the moving direction to stop imaging or perform imaging at a second time interval which is the same as or different from the first time interval when the moving speed is less than the predetermined speed, and perform additional imaging if the imaging is stopped and perform additional imaging at a third time interval shorter than the second time interval if the imaging at the second time interval is in execution when the moving speed is greater than or equal to the predetermined speed from the second wireless communication interface, which receives the first image data and the second image data from the capsule endoscope, to the capsule endoscope.

DETAILED DESCRIPTION OF THE PREFERRED EMBODIMENTS

Hereinafter, embodiments of the present invention will be described with reference to the drawings.

First Embodiment

First, the first embodiment of the present invention will be described. In this embodiment, an example of a capsule endoscope system having a binocular capsule endoscope configured to transmit image data after imaging through wireless communication to a reception apparatus and the reception apparatus configured to receive image data transmitted from the capsule endoscope, detect a moving speed of the capsule endoscope from the image data, and instruct the capsule endoscope to execute additional imaging when the moving speed is greater than or equal to a predetermined speed will be described. The capsule endoscope of this embodiment normally images only an imaging range of a moving direction (front direction) and performs additional imaging of an imaging range of a backward direction (rear direction) when the moving speed of the capsule endoscope, that is, the speed of movement, is greater than or equal to a predetermined speed. Detection of the moving speed of the capsule endoscope is performed using image data generated by the imaging of the imaging range of the moving direction.

[System Configuration]

Figure 1:
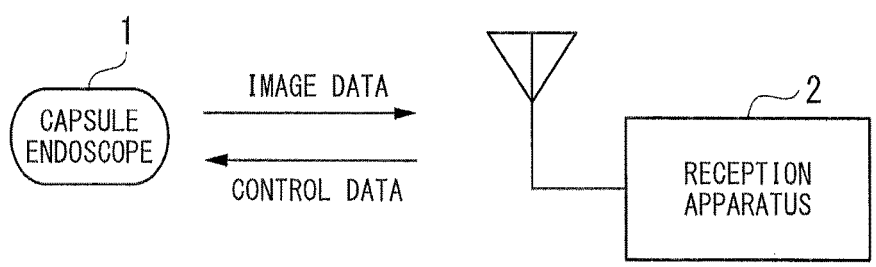
FIG. 1 is a block diagram illustrating a configuration example of a capsule endoscope system according to a first embodiment of the present invention.
Figure 2:
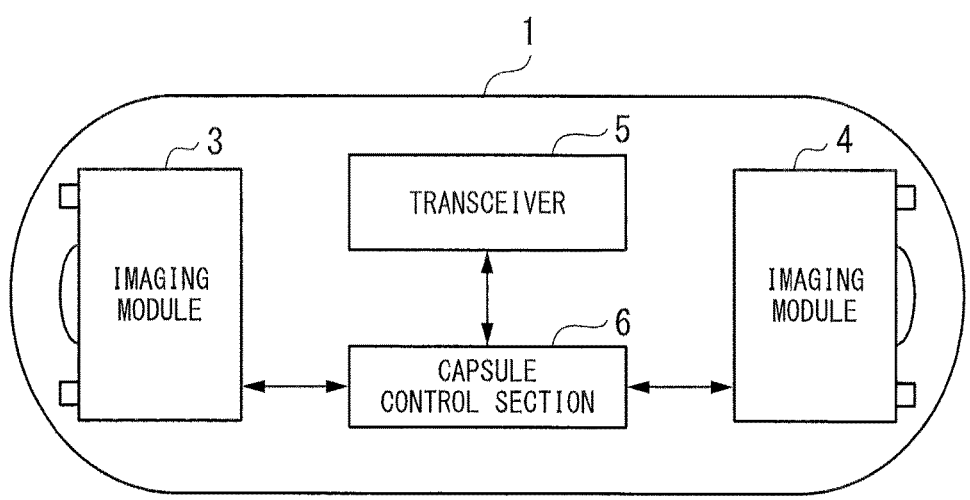
FIG. 2 is a block diagram illustrating a configuration example of the capsule endoscope according to the first embodiment of the present invention.
Figure 3:
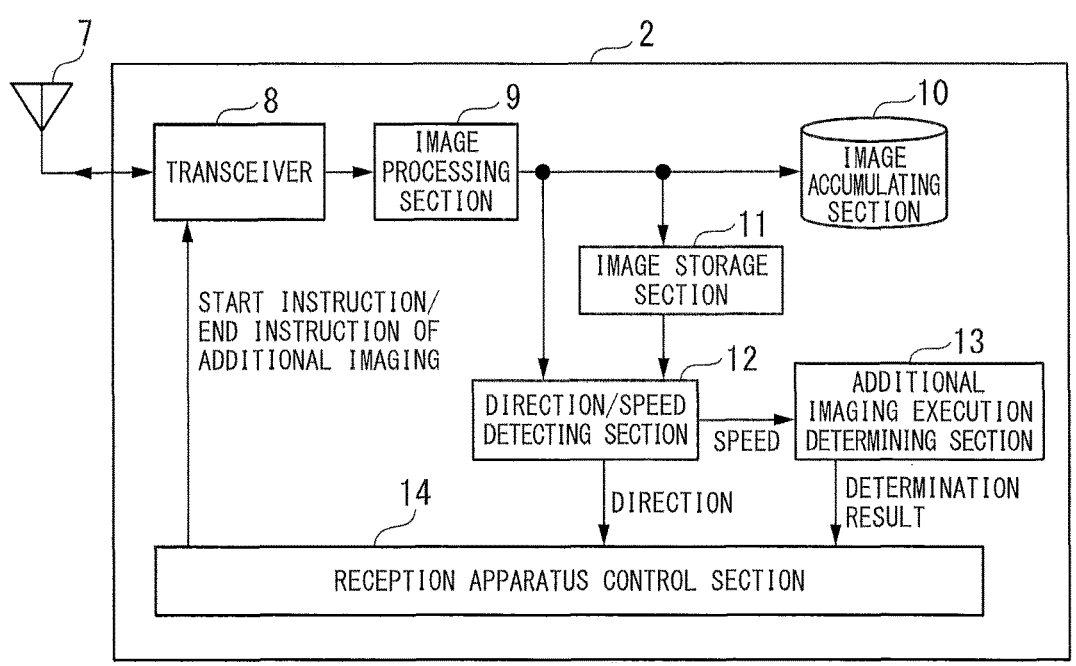
FIG. 3 is a block diagram illustrating a configuration example of a reception apparatus according to the first embodiment of the present invention.
Figure 4:
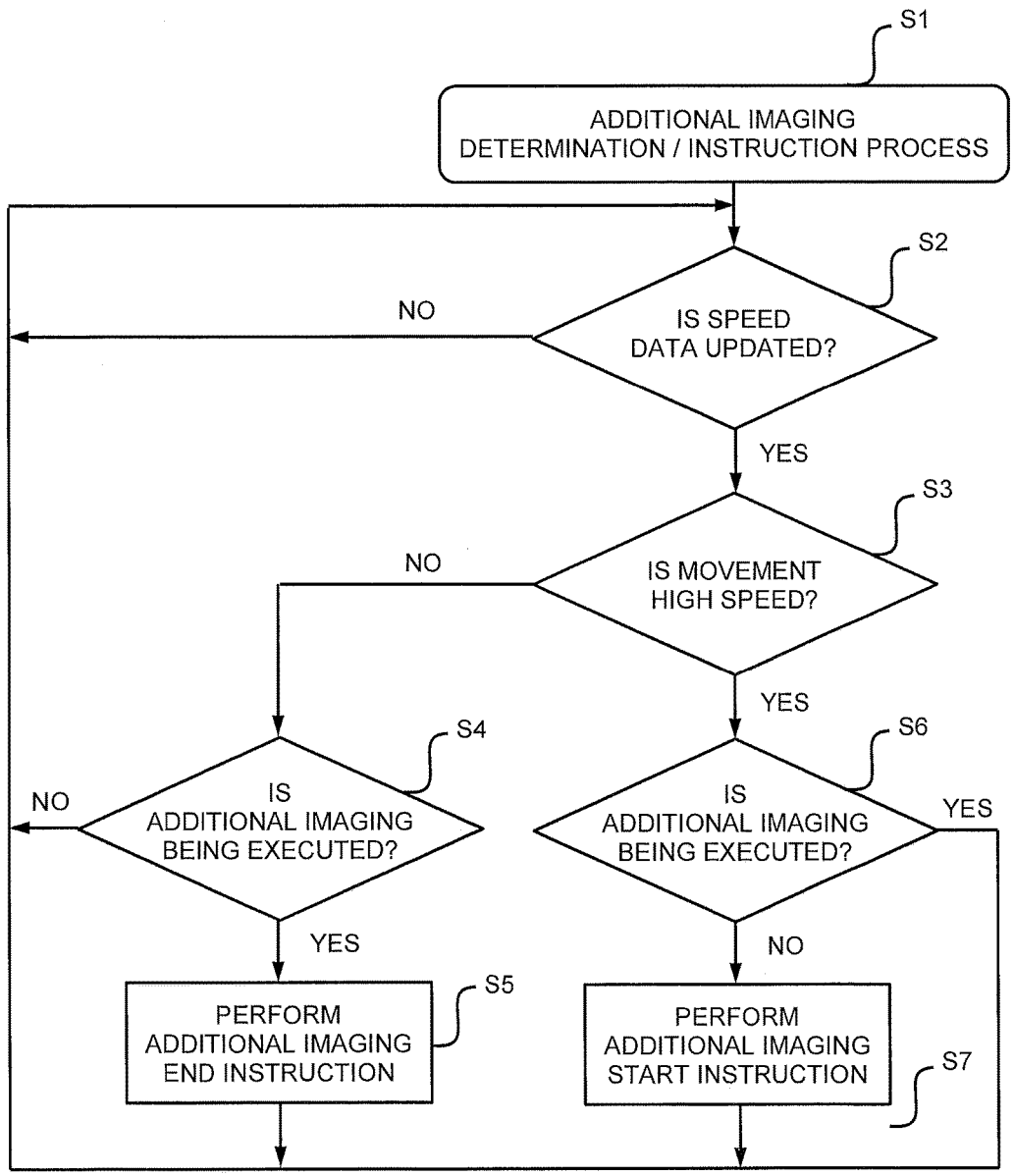
FIG. 4 is a flowchart illustrating a procedure of an additional imaging determination/instruction process performed by the reception apparatus according to the first embodiment of the present invention.

Configurations of the capsule endoscope system, the capsule endoscope 1, and the reception apparatus 2 and outlines of operations of the capsule endoscope 1 and the reception apparatus 2 will be described using FIGS. 1 to 4. FIG. 1 is a block diagram illustrating a configuration example of the capsule endoscope system according to this embodiment. FIG. 2 is a block diagram illustrating a configuration example of the capsule endoscope 1 according to this embodiment. FIG. 3 is a block diagram illustrating a configuration example of the reception apparatus 2 according to this embodiment. FIG. 4 is a flowchart illustrating a procedure of a process performed by the reception apparatus 2 and related to a determination of whether to perform additional imaging and an instruction of the additional imaging according to this embodiment.

As illustrated in FIG. 1, the capsule endoscope system of this embodiment has the capsule endoscope 1 and the reception apparatus 2. The capsule endoscope 1 and the reception apparatus 2 are connected by wireless communication. The capsule endoscope 1 is inserted into a living body (human body) and image data obtained through imaging is wirelessly transmitted. The wirelessly transmitted image data is received by an antenna within the reception apparatus 2. A reception process is performed on the received image data. The reception apparatus 2 stores the received image data, detects the moving direction and the moving speed of the capsule endoscope 1 from the image data, and controls an imaging state of the capsule endoscope 1 by wirelessly transmitting control data (various types of instruction data to be described later) to the capsule endoscope 1.

The capsule endoscope 1 has two imaging modules. As illustrated in FIG. 2, the imaging modules perform imaging in mutually opposite directions. The reception apparatus 2 detects the moving direction of the capsule endoscope 1 and instructs the capsule endoscope 1 to image the imaging range of the moving direction in normal imaging. In addition, when it is determined that the moving speed of the capsule endoscope 1 is greater than or equal to the predetermined speed, the reception apparatus 2 instructs the capsule endoscope 1 to execute the additional imaging for imaging the imaging range of a direction opposite to the moving direction. Because a configuration of the capsule endoscope system other than the configuration related to the additional imaging is well known, further description thereof will be omitted.

[Configuration/Operation of Each Apparatus]

As illustrated in FIG. 2, the capsule endoscope 1 has an imaging module 3, an imaging module 4, a transceiver 5, and a capsule control section 6.

The imaging modules 3 and 4 are imaging modules configured to perform an imaging process and output image data and have a lens, an imaging element, and a light-emitting diode (LED) element for illumination. Because the imaging module for the capsule endoscope is well known, description thereof will be omitted.

The imaging modules 3 and 4 are disposed on both ends (a first end and a second end different from the first end) of a main body of the capsule endoscope 1 so that imaging surfaces of the imaging modules 3 and 4 face away from each other. The imaging module 3 is disposed on the first end of the capsule endoscope 1 so that an imaging direction becomes an outward direction. The imaging module 4 is disposed so that the imaging direction is an outward direction, that is, a direction which is substantially opposite to the image direction of the imaging module 3, on the second end of the capsule endoscope 1. In addition, the imaging modules 3 and 4 are disposed so that the imaging directions are substantially the same as a moving direction or a backward direction of the capsule endoscope 1. A sectional external shape of the capsule endoscope 1 has two straight lines which are substantially parallel and two curves which are opposite. The imaging modules 3 and 4 are disposed so that the imaging directions are substantially parallel to the two straight lines.

One of the imaging modules 3 and 4 serves as a first imaging module configured to image a first imaging range and output first image data by directing the imaging direction in a first direction, and the other serves as a second imaging module configured to image a second imaging range that does not overlap the first imaging range and output second image data by directing the imaging direction in a second direction different from the first direction. In addition, one of the imaging modules 3 and 4 serves as an imaging module having the imaging direction closer to the moving direction (or the imaging direction which is substantially the same as the moving direction), and the other serves as an imaging module having the imaging direction farther from the moving direction (or the imaging direction which is substantially opposite to the moving direction). If the imaging direction is closer to the moving direction, this means that an angle formed by the imaging direction and the moving direction is relatively small. In addition, if the imaging direction is farther from the moving direction, this means that the angle formed by the imaging direction and the moving direction is relatively large.

The transceiver 5 performs wireless communication with the reception apparatus 2. The transceiver 5 is a first wireless communication interface configured to transmit image data output from the imaging modules 3 and 4 to the reception apparatus 2 and receive instruction data for controlling operations of the imaging modules 3 and 4 from the reception apparatus 2. When the instruction data is received by the transceiver 5, the capsule control section 6 controls the imaging modules 3 and 4 based on the instruction data. The image data output from the imaging modules 3 and 4 is input to the capsule control section 6 and converted into communication data by the capsule control section 6. This data is wirelessly transmitted to the reception apparatus 2 via the transceiver 5.

In addition, the capsule control section 6 stores a program and necessary data for controlling an operation of the capsule control section 6. A function of the capsule control section 6, for example, can be implemented as a function of software by causing a computer of the capsule endoscope 1 to read and execute a program including a command for prescribing the operation of the capsule control section 6. In addition, this program, for example, may be provided by a "computer-readable recording medium" such as a flash memory. In addition, the above-described program may be input to the capsule endoscope 1 when the program is transmitted from a computer in which the program is stored in a storage apparatus or the like to the capsule endoscope 1 via a transmission medium or through transmission waves of the transmission medium. Here, the "transmission medium" for transmitting the program includes a medium having a function of transmitting information, such as a network (communication network) like the Internet or a communication circuit (communication line) like a telephone circuit. In addition, the above-described program may implement some of the above-described functions. Further, the above-described program may be a program, i.e., a so-called differential file (differential program), capable of implementing the above-described function in combination with a program already recorded on the computer system.

As illustrated in FIG. 3, the reception apparatus 2 has an antenna 7, a transceiver 8, an image processing section 9, an image accumulating section 10, an image storage section 11, a direction/speed detecting section 12, an additional imaging execution determining section 13, and a reception apparatus control section 14.

The transceiver 8 performs wireless communication with the capsule endoscope 1 via the antenna 7. The transceiver 8 is a second wireless communication interface for receiving image data from the capsule endoscope 1 and transmitting the instruction data to the capsule endoscope 1. The image processing section 9 performs image processing such as color conversion on image data received by the transceiver 8. Image data processed by the image processing section 9 is output to the image accumulating section 10, the image storage section 11, and the direction/speed detecting section 12.

The image accumulating section 10 is a storage module configured to accumulate image data processed by the image processing section 9 for a plurality of frames in units of frames. The image storage section 11 is a storage module configured to store image data processed by the image processing section 9 for one frame.

The direction/speed detecting section 12 performs a process of detecting the moving direction and the moving speed of the capsule endoscope 1 from image data (first or second image data). Specifically, the direction/speed detecting section 12 detects the moving direction and the moving speed from image data of a current frame output from the image processing section 9 and image data of a previous frame output from the image storage section 11. There is a technique using moving vector detection or the like in an algorithm of detecting the moving direction and the moving speed from image data of two of different frames. Because details of the technique are well known, description thereof will be omitted here. The data of the two images for use in detection of the moving direction and the moving speed by the direction/speed detecting section 12 is image data output from the same imaging module. The direction/speed detecting section 12 detects the moving direction and the moving speed of the capsule endoscope 1 from the image data output from the imaging module 3 or 4 of the capsule endoscope 1.

In this embodiment, the moving direction of the capsule endoscope 1 is sensed in the step of starting an inspection. Thereafter, the imaging module imaging the imaging range of the moving direction is selected and image data output by the imaging module is transmitted to the reception apparatus 2. In the reception apparatus 2, the moving direction and the moving speed are detected from the received image data.

When the moving direction of the capsule endoscope 1 has changed during the inspection, it is detected that the moving direction has changed from the captured image data and the imaging module to image the imaging range of the moving direction is switched, so that the imaging continues. In addition, when the capsule endoscope 1 moves at a high speed and a correlation of image data of two frames is lost, it is difficult to detect the moving speed. Thus, the direction/speed detecting section 12 determines that the moving speed of the capsule endoscope 1 is a highest speed. Direction data indicating the moving direction detected by the direction/speed detecting section 12 is output to the reception apparatus control section 14. In addition, speed data indicating the moving speed detected by the direction/speed detecting section 12 is output to the additional imaging execution determining section 13.

The additional imaging execution determining section 13 determines whether the moving speed indicated by the speed data output from the direction/speed detecting section 12 is greater than or equal to a predetermined speed, and determines whether to perform additional imaging by the imaging module configured to image the imaging range of a direction different from the moving direction according to the determination result. Determination result data indicating a result of the determination by the additional imaging execution determining section 13 is output to the reception apparatus control section 14.

The reception apparatus control section 14 controls each section within the reception apparatus 2. In addition, the reception apparatus control section 14 performs control to be described later. The reception apparatus control section 14 finds an imaging module outputting image data used in detection of the moving direction and the moving speed. Based on a relationship between the imaging direction of the imaging module and the moving direction indicated by the direction data output from the direction/speed detecting section 12, the reception apparatus control section 14 selects the imaging module configured to image the imaging range of the moving direction between the imaging modules 3 and 4.

For example, when the moving direction is different from the imaging direction, the reception apparatus control section 14 selects an imaging module different from the imaging module outputting image data used in the detection of the moving direction and the moving speed. In addition, when the moving direction is the same as the imaging direction, the reception apparatus control section 14 selects the imaging module outputting the image data used in the detection of the moving direction and the moving speed.

The reception apparatus control section 14 generates indication data indicating the imaging module configured to image the imaging range of the moving direction and transmits the indication data from the transceiver 8 to the capsule endoscope 1. After the transmitted indication data is received by the transceiver 5 of the capsule endoscope 1, the indication data is output to the capsule control section 6. The capsule control section 6 selects the imaging module configured to image the imaging range of the moving direction based on the indication data.

In addition, the reception apparatus control section 14 instructs the imaging module having the imaging direction closer to the moving direction between the imaging modules 3 and 4 to perform imaging at a first time interval. In addition, as will be described later, the reception apparatus control section 14 instructs the imaging module having the imaging direction farther from the moving direction to stop imaging when the moving speed is less than the predetermined speed. In addition, the reception apparatus control section 14 instructs the imaging module having the imaging direction farther from the moving direction to perform additional imaging if the imaging is stopped when the moving speed is greater than or equal to the predetermined speed.

The reception apparatus control section 14 generates instruction data indicating a start instruction of the additional imaging when the additional imaging starts, generates instruction data indicating an end instruction of the additional imaging when the additional imaging ends, and transmits the instruction data from the transceiver 8 to the capsule endoscope 1. After the transmitted instruction data is received by the transceiver 5 of the capsule endoscope 1, the instruction data is output to the capsule control section 6 and used in control of the additional imaging.

When the instruction data indicating the start instruction of the additional imaging is received, the capsule endoscope 1 starts the imaging of the imaging range of a direction opposite to the moving direction by the imaging module different from the imaging module that is imaging the imaging range of the moving direction. The additional imaging in this embodiment is performed in a predetermined cycle shorter than a cycle of the imaging of the moving direction and continues until instruction data indicating the end instruction of the additional imaging is received.

In addition, the reception apparatus control section 14 stores a program or necessary data for controlling an operation of the reception apparatus control section 14. A process of implementing functions of the direction/speed detecting section 12 and the additional imaging execution determining section 13 may be performed by the reception apparatus control section 14. A function of the reception apparatus control section 14, for example, can be implemented as a function of software by causing a computer of the reception apparatus 2 to read and execute a program including a command for prescribing the operation of the reception apparatus control section 14. A method of installing the program may be similar to a method of installing a program for controlling the operation of the capsule control section 6 of the capsule endoscope 1.

FIG. 4 illustrates a procedure of an additional imaging determination/instruction process S1 related to a determination of whether to perform the additional imaging and an instruction of the additional imaging to be performed by the reception apparatus 2. The additional imaging determination/instruction process S1 is a process of generating the instruction data indicating the start instruction or the end instruction of the additional imaging based on the speed data from the direction/speed detecting section 12.

In the additional imaging determination/instruction process S1, the following process is performed. First, the additional imaging execution determining section 13 performs speed data update waiting S2 for waiting for the speed data output from the direction/speed detecting section 12 to be updated.

After the speed data is updated, the additional imaging execution determining section 13 makes a high-speed movement determination S3 for comparing the updated speed data to the predetermined speed and determining whether the moving speed indicated by the speed data is greater than or equal to the predetermined speed. When the moving speed is less than a predetermined speed (also including a still state in which the moving speed is 0), it is determined that the capsule endoscope 1 is moving at a low speed. When the movement speed is greater than or equal to the predetermined speed, it is determined that the capsule endoscope 1 is moving at a high speed.

When it is determined that the capsule endoscope 1 is moving at the low speed, the additional imaging execution determining section 13 makes an additional imaging execution determination S4, for determining whether the additional imaging is in execution. The additional imaging execution determining section 13 stores information indicating a current state of the imaging by the capsule endoscope 1 and makes the determination based on the information. When it is determined that the current state is a state in which the additional imaging is stopped, speed data update waiting S2 is performed. In addition, when it is determined that the current state is a state in which the additional imaging is in execution, the additional imaging execution determining section 13 outputs determination result data indicating the end of the additional imaging.

The reception apparatus control section 14 performs an additional imaging end instruction S5 for instructing the capsule endoscope 1 to end the additional imaging based on the determination result data output from the additional imaging execution determining section 13. In the additional imaging end instruction S5, the reception apparatus control section 14 generates instruction data indicating the end instruction of the additional imaging and transmits the instruction data from the transceiver 8 to the capsule endoscope 1. The capsule control section 6 of the capsule endoscope 1 instructs the imaging module having the imaging direction farther from the moving direction to stop the imaging based on the instruction data received by the transceiver 5. The capsule control section 6 stores information of the imaging module that performs the additional imaging and instructs the imaging module indicated by the information to stop the imaging. When the additional imaging end instruction S5 is performed, the information indicating the current state of the imaging by the capsule endoscope 1 stored by the additional imaging execution determining section 13 is updated to a value indicating that the additional imaging is stopped. After the additional imaging end instruction S5, the speed data update waiting S2 is performed.

When it is determined that the capsule endoscope 1 is moving at the high speed in the high-speed movement determination S3, the additional imaging execution determining section 13 makes an additional imaging execution determination S6 for determining whether the additional imaging is in execution. As described above, the additional imaging execution determining section 13 makes the determination based on the information indicating the current state of the imaging by the capsule endoscope 1. When it is determined that the current state is a state in which the additional imaging is in execution, the speed data update waiting S2 is performed. In addition, when it is determined that the current state is a state in which the additional imaging is stopped, the additional imaging execution determining section 13 outputs determination result data indicating the start of the additional imaging.

The reception apparatus control section 14 performs an additional imaging start instruction S7 for instructing the capsule endoscope 1 to start the additional imaging based on the determination result data output from the additional imaging execution determining section 13. In the additional imaging start instruction S7, the reception apparatus control section 14 generates instruction data indicating the start instruction of the additional imaging and transmits the instruction data from the transceiver 8 to the capsule endoscope 1. The capsule control section 6 of the capsule endoscope 1 instructs the imaging module having the imaging direction farther from the moving direction to perform the additional imaging based on the instruction data received by the transceiver 5. That is, the capsule control section 6 instructs the imaging module stopping the imaging to perform the additional imaging. When the additional imaging start instruction S7 is performed, the information indicating the current state of the imaging by the capsule endoscope 1 stored by the additional imaging execution determining section 13 is updated to a value indicating that the additional imaging is in execution. In addition, the capsule control section 6 updates information of the imaging module that performs the additional imaging. After the additional imaging start instruction S7, the speed data update waiting S2 is performed.

[Specific Operation of Additional Imaging]

Figure 5:
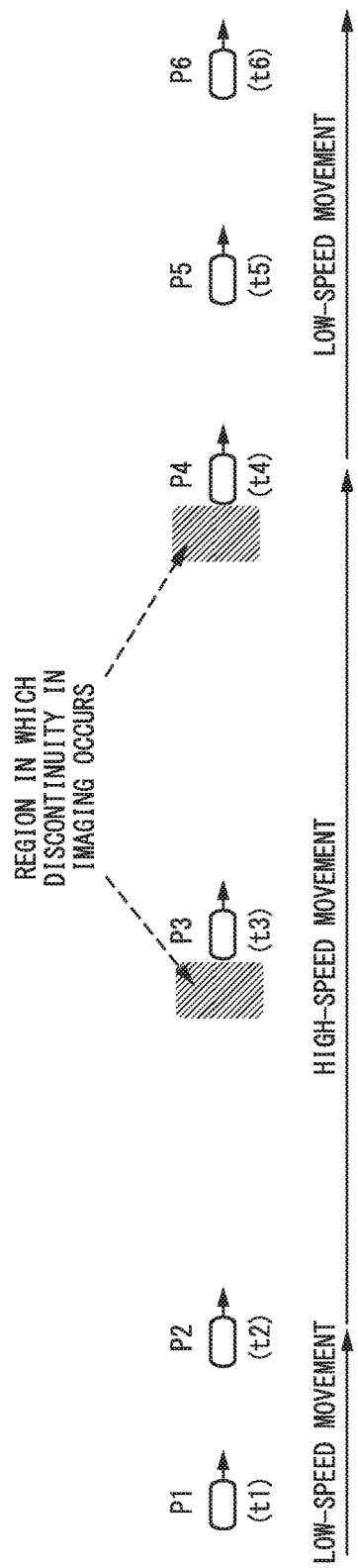
FIG. 5 is a reference diagram illustrating a position at which the capsule endoscope performs imaging and an imaging direction when no additional imaging is performed in the first embodiment of the present invention.
Figure 6:
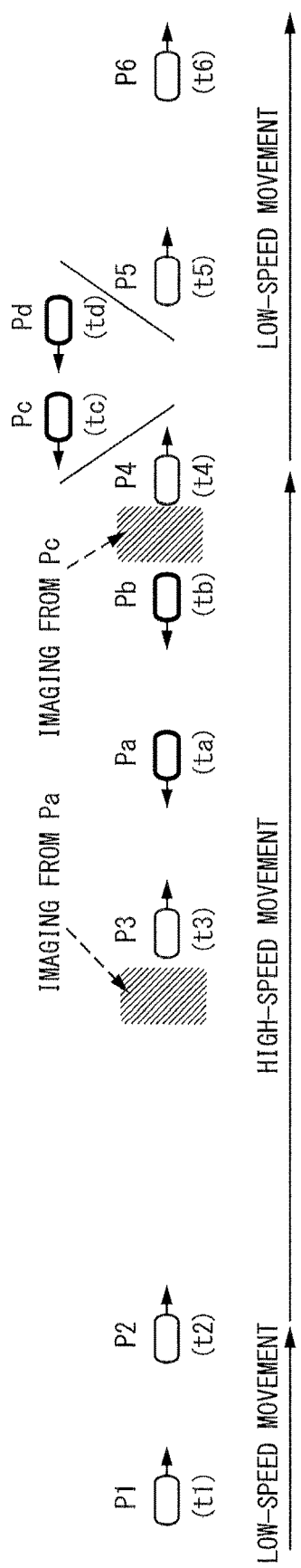
FIG. 6 is a reference diagram illustrating a position at which the capsule endoscope performs imaging and an imaging direction when the additional imaging is performed in the first embodiment of the present invention.

A specific operation of the start/end of the additional imaging will be described using FIGS. 5 to 8. FIGS. 5 and 6 illustrate states of imaging when the capsule endoscope moves from a low-speed movement state to a high-speed movement state and then returns to the low-speed movement state based on a position of the capsule endoscope. In FIGS. 5 and 6, the capsule endoscope moves from the left to the right.

Figure 7:
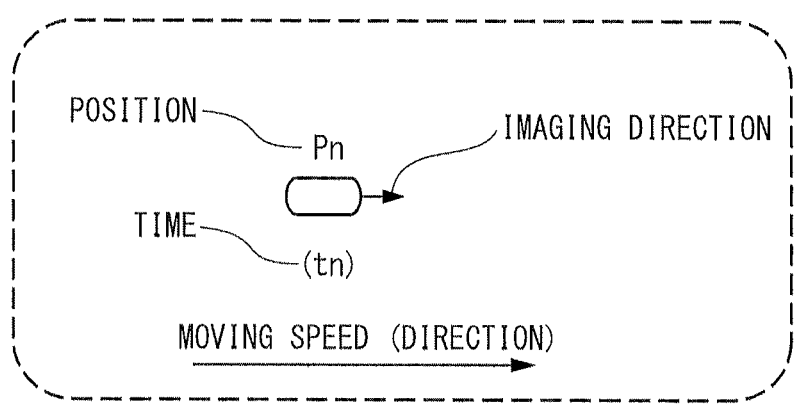
FIG. 7 is a reference diagram illustrating a notation method of a position at which the capsule endoscope performs imaging and an imaging direction in the first embodiment of the present invention.

FIG. 7 illustrates a notation method of a position at which the capsule endoscope performs imaging and an imaging direction in FIGS. 5 and 6. As illustrated in FIG. 7, an arrow indicating the imaging direction is drawn on the right side of an elliptic figure schematically indicating the position of the capsule endoscope at each point in time at which imaging is performed. In addition, a symbol Pn indicating the position of the capsule endoscope is drawn on the upper side of the elliptic figure and a symbol to indicating the time is drawn on the lower side of the elliptic figure.

FIG. 5 illustrates a position at which the capsule endoscope performs imaging and an imaging direction according to a conventional process in which no additional imaging is performed. FIG. 6 illustrates a position at which the capsule endoscope 1 performs imaging and an imaging direction according to this embodiment when the moving speed changes like the moving speed illustrated in FIG. 5.

In the present description, as illustrated in FIG. 5, the capsule endoscope moves at a low speed between positions P1 and P2, moves at a high speed between positions P2 and P4, and moves at a low speed between positions P4 and P6. In the conventional process in which no additional imaging is performed, only imaging of an imaging range of the moving direction is performed at positions P1 to P6 illustrated in FIG. 5. In this case, there is a region in which discontinuity in the imaging occurs between the positions P2 and P4 at which the capsule endoscope moves at the high speed. When the capsule endoscope moves as illustrated in FIG. 5, the discontinuity in the imaging occurs in left regions of the positions P3 and P4.

In FIG. 6, a position at which the capsule endoscope 1 performs imaging when the additional imaging is performed is illustrated. In the present description, the additional imaging is performed at positions Pa, Pb, Pc, and Pd. Although the positions Pc and Pd are extracted and illustrated on the upper portion for convenience of illustration in FIG. 6, the positions Pc and Pd are originally between the positions P4 and P5. In this embodiment, the additional imaging is performed twice between the positions P3 and P4 and performed twice between the positions P4 and P5.

As illustrated in FIG. 6, the left region of the position P3 at which the discontinuity in the imaging occurs in FIG. 5 is imaged by additional imaging performed at the position Pa. In addition, the left region of the position P4 at which the discontinuity in the imaging occurs in FIG. 5 is imaged by additional imaging performed at the position Pc. Thus, it is possible to eliminate the discontinuity in the imaging.

Figure 8:
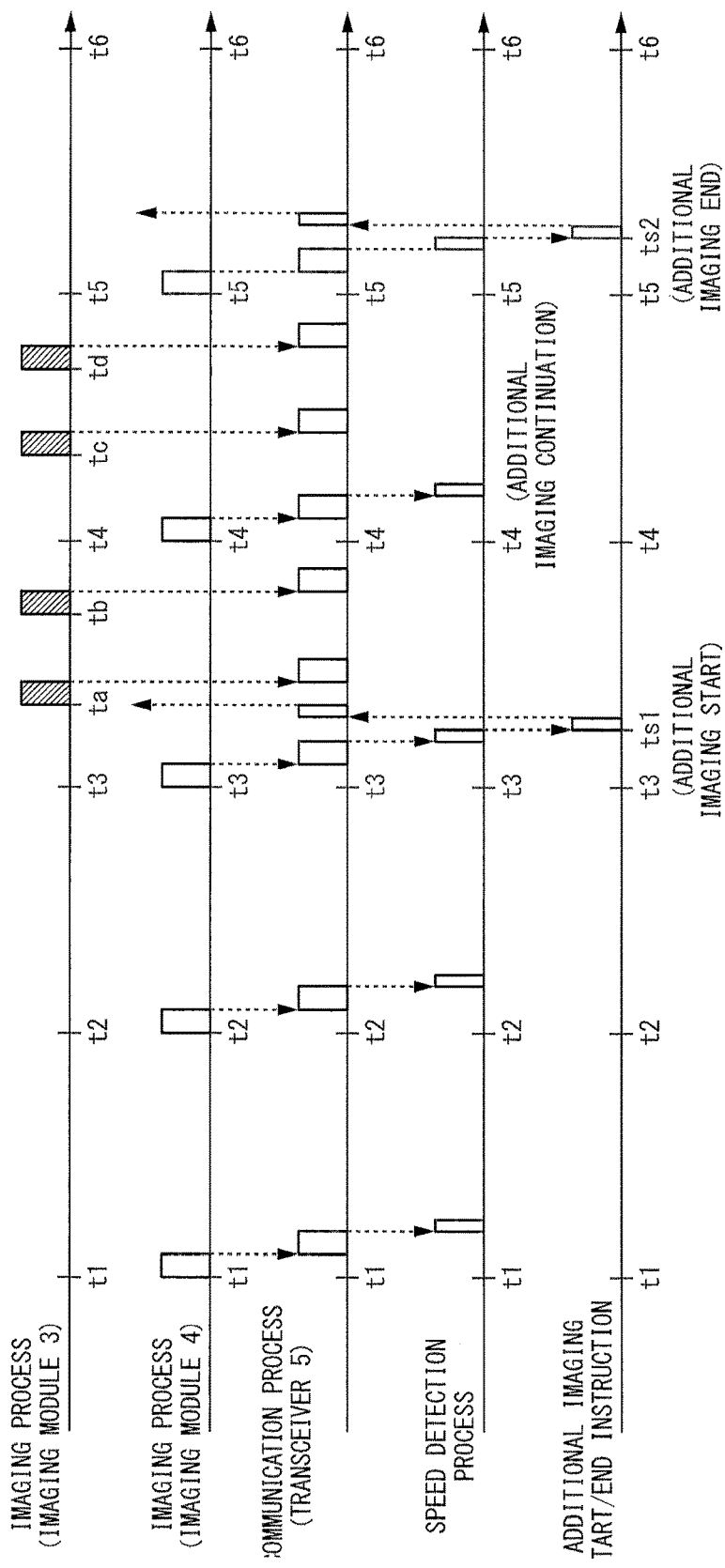
FIG. 8 is a timing chart illustrating timings of processing performed by the capsule endoscope and the reception apparatus in the first embodiment of the present invention.

FIG. 8 is a timing chart illustrating timings of various types of processing performed by the capsule endoscope 1 and the reception apparatus 2 when the capsule endoscope 1 moves at the moving speed illustrated in FIG. 6. FIG. 8 illustrates processing performed by the capsule endoscope 1 and the reception apparatus 2 at each time point illustrated in FIG. 6 using the passage of time as a reference (horizontal axis).

A procedure of executing the additional imaging will be described using FIG. 8. In FIG. 8, timings of imaging processes by the imaging modules 3 and 4 of the capsule endoscope 1, a timing of a communication process performed between the transceiver 5 of the capsule endoscope 1 and the transceiver 8 of the reception apparatus 2, a timing of a speed detecting process performed by the direction/speed detecting section 12, and a timing at which instruction data indicating a start instruction or an end instruction of the additional imaging is output from the reception apparatus control section 14 based on a determination result of the additional imaging execution determining section 13 are illustrated.

In FIG. 8, the imaging module 4 images the imaging range of the moving direction. In FIG. 8, the imaging module 4 starts imaging at each of timings t1 to t6. As illustrated, after the imaging process by the imaging module 4 ends, the communication process by the transceiver 5 is performed and the speed detecting process by the direction/speed detecting section 12 is further performed.

As illustrated in FIG. 6, the capsule endoscope 1 moves at a high speed between the positions P2 and P4. The start of the high-speed movement by the capsule endoscope 1 is detected by comparing image data generated at the timings t2 and t3. Thus, the timing at which the instruction data indicating the start instruction of the additional imaging is generated becomes a timing ts1 immediately after the timing t3.

When the instruction data indicating the start instruction of the additional imaging is received, the capsule endoscope 1 starts the additional imaging using the imaging module 3. At timings to and tb between the timings t3 and t4 and timings tc and td between the timings t4 and t5, additional imaging by the imaging module 3 is performed. From the relationship of power consumption or resources of various types of processing, the additional imaging by the imaging module 3 is performed as long as possible at the timing at which the additional imaging does not overlap imaging by the imaging module 4, that is, in a free time of imaging by the imaging module 4. Thus, as illustrated in FIG. 8, the additional imaging is performed twice when two additional imaging operations are possible during normal imaging. In addition, the normal imaging may be time-consuming and the additional imaging operation may be performed only once. It is not what an imaging rate proportional to the moving speed is set and the additional imaging is performed at the imaging rate.

In the comparison of the image data generated at the timings t3 and t4, it is detected that the capsule endoscope 1 moves at the high speed. Thus, the additional imaging by the imaging module 3 continues.

After the capsule endoscope 1 moves at the high speed, the capsule endoscope 1 moves at a low speed between the positions P4 and P6. The start of the low-speed movement by the capsule endoscope 1 is detected by comparing image data generated at the timings t4 and t5. Thus, the timing at which the instruction data indicating the end instruction of the additional imaging is generated becomes a timing ts2 immediately after the timing t5.

As a system to be derived in this embodiment, there is a system in which the capsule endoscope 1 performs additional imaging only once when instruction data indicating the start instruction of the additional imaging is received and does not perform the additional imaging until instruction data indicating the start instruction of the additional imaging is received the next time. This serves as a system focusing on suppressing power consumption by the additional imaging.

In this system, in the case of FIG. 6, the additional imaging is performed only at the position Pa. Even in this case, it is possible to perform the additional imaging in a region of a widest range in which discontinuity in imaging occurs immediately after high-speed movement starts.

In this embodiment, the capsule control section 6, the image processing section 9, the image accumulating section 10, and the image storage section 11 are not essential components for obtaining a characteristic effect of the capsule endoscope system according to this embodiment.

According to this embodiment, a capsule endoscope system is configured to include: the capsule endoscope 1 having a first imaging module (imaging module 3 or 4) configured to direct an imaging direction in a first direction, image a first imaging range, and output first image data; a second imaging module (imaging module 3 or 4) configured to direct an imaging direction in a second direction different from the first direction, image a second imaging range that does not overlap the first imaging range, and output second image data; and a first wireless communication interface (transceiver 5) configured to transmit the first image data and the second image data; and the reception apparatus 2 having a second wireless communication interface (transceiver 8) configured to receive the first image data and the second image data, wherein the reception apparatus 2 has a moving direction detecting section (direction/speed detecting section 12) configured to detect a moving direction of the capsule endoscope 1; a moving speed detecting section (direction/speed detecting section 12) configured to detect a moving speed of the capsule endoscope 1; a speed determining section (additional imaging execution determining section 13) configured to determine whether the moving speed is greater than or equal to a predetermined speed; and an imaging instruction section (reception apparatus control section 14) configured to instruct an imaging module having an imaging direction closer to a moving direction between the first and second imaging modules to perform imaging at a first time interval and instruct an imaging module having an imaging direction farther from the moving direction to stop imaging when the moving speed is less than the predetermined speed and perform additional imaging if the imaging is stopped when the moving speed is greater than or equal to the predetermined speed.

In addition, according to this embodiment, the reception apparatus 2 is configured to include: a second wireless communication interface (transceiver 8) configured to receive first image data and second image data from the capsule endoscope 1; a moving direction detecting section (direction/speed detecting section 12) configured to detect a moving direction of the capsule endoscope 1; a moving speed detecting section (direction/speed detecting section 12) configured to detect a moving speed of the capsule endoscope 1; a speed determining section (additional imaging execution determining section 13) configured to determine whether the moving speed is greater than or equal to a predetermined speed; and an imaging instruction section (reception apparatus control section 14) configured to transmit instruction data for instructing an imaging module having an imaging direction closer to a moving direction between the first imaging module (imaging module 3 or 4) and the second imaging module (imaging module 3 or 4) to perform imaging at a first time interval and instructing an imaging module having an imaging direction farther from the moving direction to stop imaging when the moving speed is less than the predetermined speed and perform additional imaging if the imaging is stopped when the moving speed is greater than or equal to the predetermined speed from the second wireless communication interface to the capsule endoscope 1.

In addition, according to this embodiment, the imaging control method of the capsule endoscope is configured to have the step S3 of determining whether a moving speed of the capsule endoscope 1 is greater than or equal to a predetermined speed; and the step S7 of instructing an imaging module having an imaging direction closer to a moving direction between the first imaging module (imaging module 3 or 4) and the second imaging module (imaging module 3 or 4) to perform imaging at a first time interval and instructing an imaging module having an imaging direction farther from the moving direction to stop imaging when the moving speed is less than the predetermined speed and perform additional imaging if the imaging is stopped when the moving speed is greater than or equal to the predetermined speed.

In addition, according to this embodiment, a program is configured to cause a computer of the reception apparatus 2 having the second wireless communication interface to execute: the step S3 of determining whether a moving speed of the capsule endoscope 1 is greater than or equal to a predetermined speed; and the step S7 of transmitting instruction data for instructing an imaging module having an imaging direction closer to a moving direction between the first imaging module (imaging module 3 or 4) and the second imaging module (imaging module 3 or 4) to perform imaging at a first time interval and instructing an imaging module having an imaging direction farther from the moving direction to stop imaging when the moving speed is less than the predetermined speed and perform additional imaging if the imaging is stopped when the moving speed is greater than or equal to the predetermined speed from the second wireless communication interface (transceiver 8), which receives the first image data and the second image data from the capsule endoscope 1, to the capsule endoscope 1.

In this embodiment, it is possible to reduce discontinuity in imaging of a part of an imaging target occurring in association with instantaneous high-speed movement of the capsule endoscope by instructing the imaging module having the imaging direction farther from the moving direction to perform additional imaging if the imaging is stopped when the moving speed is greater than or equal to the predetermined speed.

Second Embodiment

Next, the second embodiment of the present invention will be described. In this embodiment, an example of a capsule endoscope system having a binocular capsule endoscope configured to have a built-in acceleration sensor and perform the detection of a moving speed and the determination of execution of additional imaging and a reception apparatus configured to receive image data transmitted from the capsule endoscope and store the received image data in a storage module will be described. The capsule endoscope of this embodiment is different from the capsule endoscope of the first embodiment, an imaging range of the moving direction (front direction) and an imaging range of the backward direction (rear direction) are alternately imaged at the time of low-speed movement and the imaging range of the backward direction is imaged by additional imaging at the time of high-speed movement.

Figure 9:
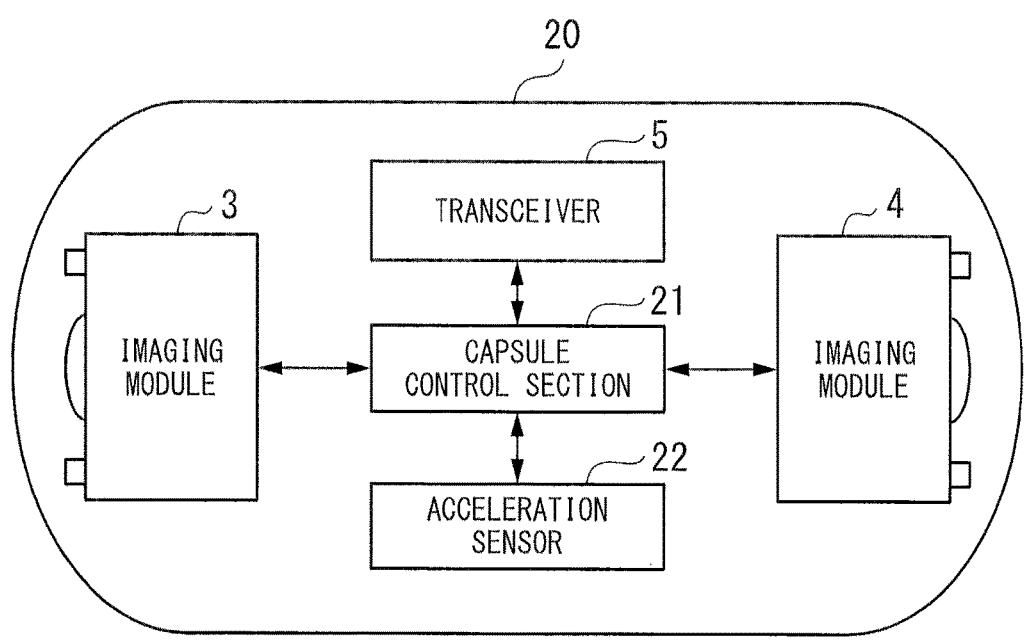
FIG. 9 is a block diagram illustrating a configuration example of a capsule endoscope according to a second embodiment of the present invention.

FIG. 9 illustrates a configuration example of the capsule endoscope 20. As illustrated in FIG. 9, the capsule endoscope 20 has an imaging module 3, an imaging module 4, a transceiver 5, a capsule control section 21, and an acceleration sensor 22. In the capsule endoscope 20 of this embodiment, the capsule control section 6 in the capsule endoscope 1 illustrated in FIG. 2 is changed to the capsule control section 21 and the acceleration sensor 22 is added.

The acceleration sensor 22 detects the acceleration of the capsule endoscope 20 and outputs acceleration data indicating the detected acceleration. The acceleration sensor 22 has an acceleration detection cycle shorter than an imaging cycle and can detect the acceleration substantially in real time. Acceleration data output from the acceleration sensor 22 is input to the capsule control section 21. Based on the acceleration data, the capsule control section 21 detects the moving direction and the moving speed of the capsule endoscope 20. Because an algorithm of detecting the moving direction and the moving speed from the acceleration data is well known, description thereof will be omitted.

As described above, the capsule endoscope 20 of this embodiment has the acceleration sensor 22 configured to detect the acceleration of the capsule endoscope 20, the capsule control section 21 detects the moving direction based on the acceleration of the capsule endoscope 20 detected by the acceleration sensor 22, and the capsule control section 21 detects the moving speed based on the acceleration of the capsule endoscope 20 detected by the acceleration sensor 22.

The capsule control section 21 performs the determination of the imaging module that images the imaging range of the moving direction and imaging control based on the detected moving direction. In addition, the capsule control section 21 performs the determination related to the execution of the additional imaging and the imaging control of the additional imaging based on the detected moving direction and moving speed.

The capsule control section 21 finds the imaging module outputting image data used in the detection of the moving direction and the moving speed. The capsule control section 21 selects the imaging module that images the imaging range of the moving direction between the imaging modules 3 and 4 based on the relationship between the imaging direction of the imaging module and the detected moving direction. The capsule control section 21 instructs the selected imaging module to perform the imaging.

In addition, the capsule control section 21 instructs an imaging module having an imaging direction closer to a moving direction between the imaging modules 3 and 4 to perform imaging at a first time interval. In addition, as will be described later, the capsule control section 21 instructs an imaging module having an imaging direction farther from the moving direction to perform imaging at a second time interval which is the same as or different from the first time interval when the moving speed is less than the predetermined speed. In addition, the capsule control section 21 instructs the imaging module to perform additional imaging at a third time interval shorter than the second time interval if the imaging at the second time interval is in execution when the moving speed is greater than or equal to the predetermined speed.

When the additional imaging starts, the capsule control section 21 instructs the imaging module having the imaging direction farther from the moving direction to start the additional imaging. In addition, when the additional imaging ends, the capsule control section 21 instructs the imaging module having the imaging direction farther from the moving direction to end the additional imaging.

In addition, the capsule control section 21 stores a program and necessary data for controlling an operation of the capsule control section 21. A function of the capsule control section 21, for example, can be implemented as a function of software by causing a computer of the capsule endoscope 20 to read and execute a program including a command for prescribing the operation of the capsule control section 21. A method of installing the program may be similar to a method of installing a program for controlling the operation of the capsule control section 6 of the capsule endoscope 1 according to the first embodiment.

In the reception apparatus 2 according to this embodiment, the image storage section 11, the direction/speed detecting section 12, and the additional imaging execution determining section 13 in the first embodiment are unnecessary. In addition, in the reception apparatus control section 14 of the reception apparatus 2, a function related to the additional imaging is unnecessary.

Figure 10:
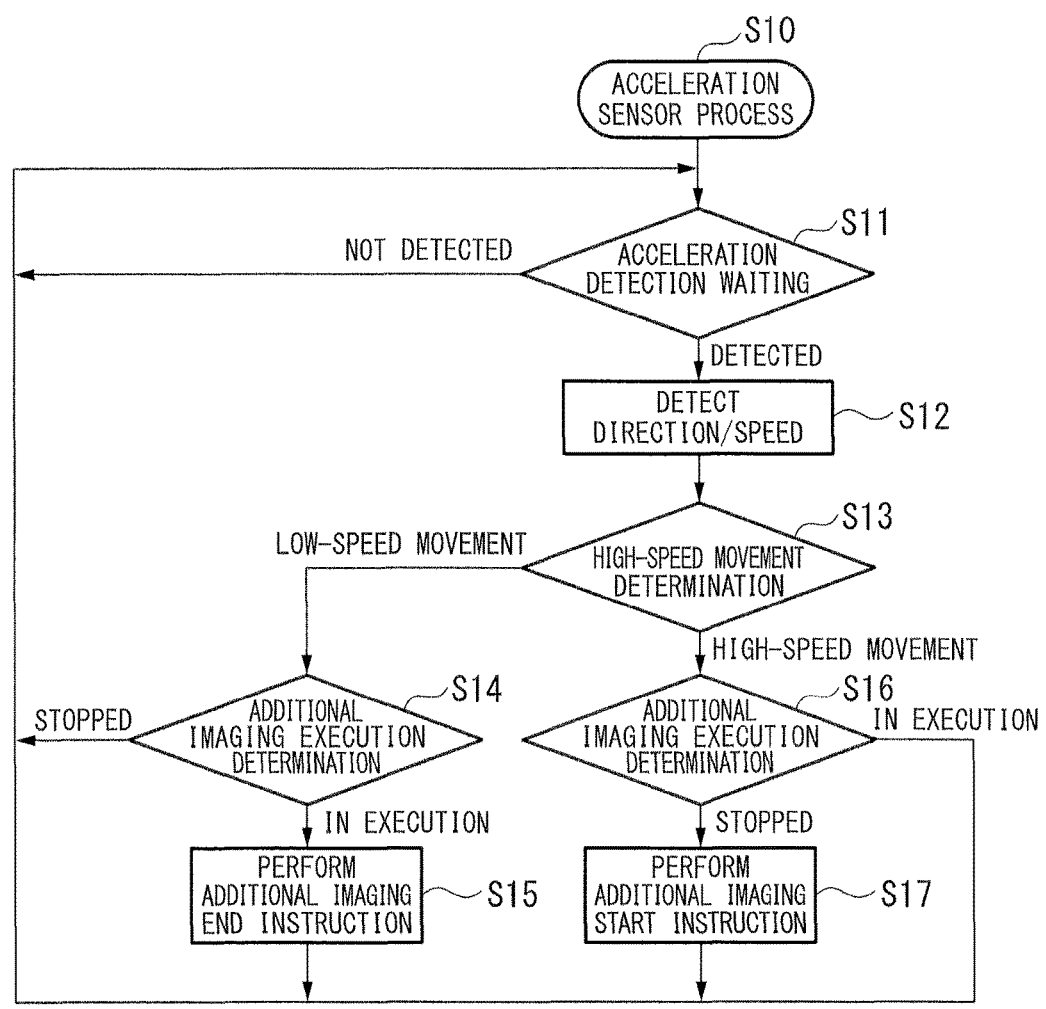
FIG. 10 is a flowchart illustrating a procedure of an acceleration sensor process performed by the capsule endoscope according to the second embodiment of the present invention.

FIG. 10 illustrates a procedure in which the capsule control section 21 performs a procedure of an acceleration sensor process S10 which is a process to be performed based on acceleration data from the acceleration sensor 22. The acceleration sensor process S10 is a process of detecting the moving direction and the moving speed of the capsule endoscope 20 and determining the start/end of the additional imaging.

In the acceleration sensor process S10, the following process is performed. First, the capsule control section 21 waits for update of the acceleration data output from the acceleration sensor 22 according to acceleration detection waiting S11 and reads the acceleration data for every predetermined cycle. The capsule control section 21 reading the acceleration data detects the moving direction and the moving speed of the capsule endoscope 20 based on the acceleration data according to direction/speed detection S12. In addition, in the direction/speed detection S12, the capsule control section 21 instructs an imaging module having an imaging direction closer to a moving direction between the first and second imaging modules 3 and 4 to perform imaging at a first time interval and instructs an imaging module having an imaging direction farther from the moving direction to perform imaging at a second time interval. Further, the capsule control section 21 stores information of the imaging module having the imaging direction farther from the moving direction, that is, the imaging module that performs the additional imaging.

Subsequently, the capsule control section 21 makes a high-speed movement determination S13 for comparing the detected moving speed to the predetermined speed and determining whether the moving speed is greater than or equal to the predetermined speed. When the moving speed is less than the predetermined speed (also including a still state), it is determined that the capsule endoscope 20 is moving at the low speed. When the moving speed is greater than or equal to the predetermined speed, it is determined that the capsule endoscope 20 is moving at the high speed.

When it is determined that the capsule endoscope 20 is moving at the low speed, the capsule control section 21 makes an additional imaging execution determination S14 for determining whether the additional imaging is in execution. The capsule control section 21 stores information indicating a current state of the imaging by the capsule endoscope 20 and makes the determination based on the information. When it is determined that the current state is a state in which the additional imaging is stopped, the acceleration detection waiting S11 is performed.

In addition, when it is determined that the current state is a state in which the additional imaging is in execution, the capsule control section 21 performs an additional imaging end instruction S15 for instructing the imaging module 3 or 4 to end the additional imaging. In this case, the imaging module indicated by information of the imaging module that performs the additional imaging is instructed to end the additional imaging. When the additional imaging end instruction S15 is performed, information indicating the current state of the imaging by the capsule endoscope 20 stored by the capsule control section 21 is updated to a value indicating that the additional imaging is stopped. After the additional imaging end instruction S15, the acceleration detection waiting S11 is performed.

When it is determined that the capsule endoscope 20 is moving at the high speed in the high-speed movement determination S13, the capsule control section 21 performs an additional imaging execution determination S16 for determining whether the additional imaging is in execution. As described above, the capsule control section 21 makes a determination based on the information indicating the current state of the imaging by the capsule endoscope 20. When it is determined that the current state is a state in which the additional imaging is in execution, the acceleration detection waiting S11 is performed.

In addition, when it is determined that the current state is a state in which the additional imaging is stopped, the capsule control section 21 performs an additional imaging start instruction S17 for instructing the imaging module 3 or 4 to start the additional imaging. In this case, the imaging module indicated by information of the imaging module that performs the additional imaging is instructed to perform the additional imaging at a third time interval shorter than the second time interval. Even after the additional imaging starts, the imaging at the second time interval is continuously executed. When the additional imaging start instruction S17 is performed, information of the current state of the imaging by the capsule endoscope 20 stored by the capsule control section 21 is updated to a value indicating that the additional imaging is in execution. After the additional imaging start instruction S17, the acceleration detection waiting S11 is performed.

Figure 11:
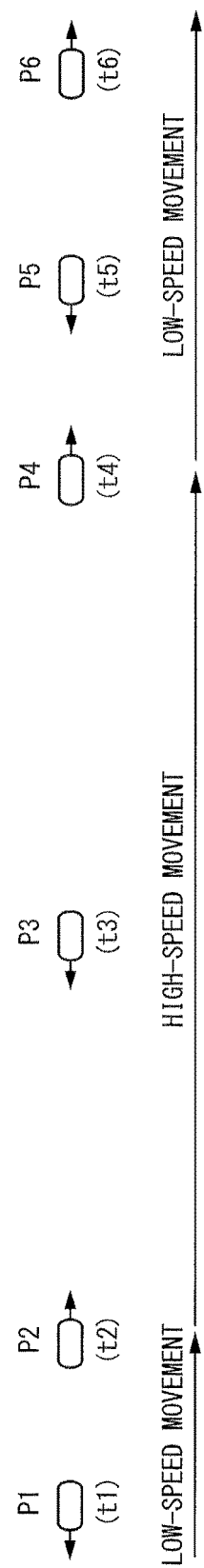
FIG. 11 is a reference diagram illustrating a position at which the capsule endoscope performs imaging and an imaging direction when no additional imaging is performed in the second embodiment of the present invention.
Figure 12:
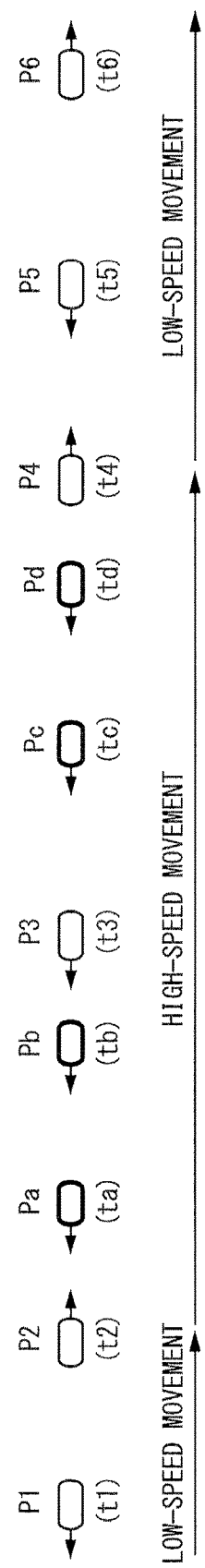
FIG. 12 is a reference diagram illustrating a position at which the capsule endoscope performs imaging and an imaging direction when the additional imaging is performed in the second embodiment of the present invention.

A specific operation of the start/end of the additional imaging will be described using FIGS. 11 to 13. FIGS. 11 and 12 illustrate states of imaging when the capsule endoscope moves from a low-speed movement state to a high-speed movement state and then returns to the low-speed movement state based on a position of the capsule endoscope. In FIGS. 11 and 12, the capsule endoscope moves from the left to the right. A notation method of a position at which the capsule endoscope performs imaging and an imaging direction in FIGS. 11 and 12 is as illustrated in FIG. 7.

FIG. 11 illustrates a position at which the capsule endoscope performs imaging and an imaging direction according to a conventional process in which no additional imaging is performed. FIG. 12 illustrates a position at which the capsule endoscope 20 performs imaging and an imaging direction according to this embodiment when the moving speed is changed like the moving speed illustrated in FIG. 11. This embodiment is different from the first embodiment in that the imaging direction is alternately changed.

In the present description, as illustrated in FIG. 11, the capsule endoscope moves at a low speed between positions P1 and P2, moves at a high speed between positions P2 and P4, and moves at a low speed between positions P4 and P6. In the conventional process in which no additional imaging is performed, there is a region in which discontinuity in the imaging occurs at an intermediate position of the positions P2 and P3 and between the positions P3 and P4 illustrated in FIG. 11.

In FIG. 12, a position at which the capsule endoscope 20 performs imaging when the additional imaging is performed is illustrated. In the present description, the additional imaging is performed at positions Pa, Pb, Pc, and Pd. In this embodiment, the additional imaging is performed twice between the positions P2 and P3 and performed twice between the positions P3 and P4.

As illustrated in FIG. 12, a region of the intermediate position of the positions P2 and P3 at which the discontinuity in the imaging occurs in FIG. 11 is imaged by the additional imaging performed at the position Pb. In addition, a region between the positions P3 and P4 at which the discontinuity in imaging occurs in FIG. 11 is imaged by the additional imaging performed at the positions Pc and Pd. Thus, it is possible to eliminate the discontinuity in the imaging.

Figure 13:
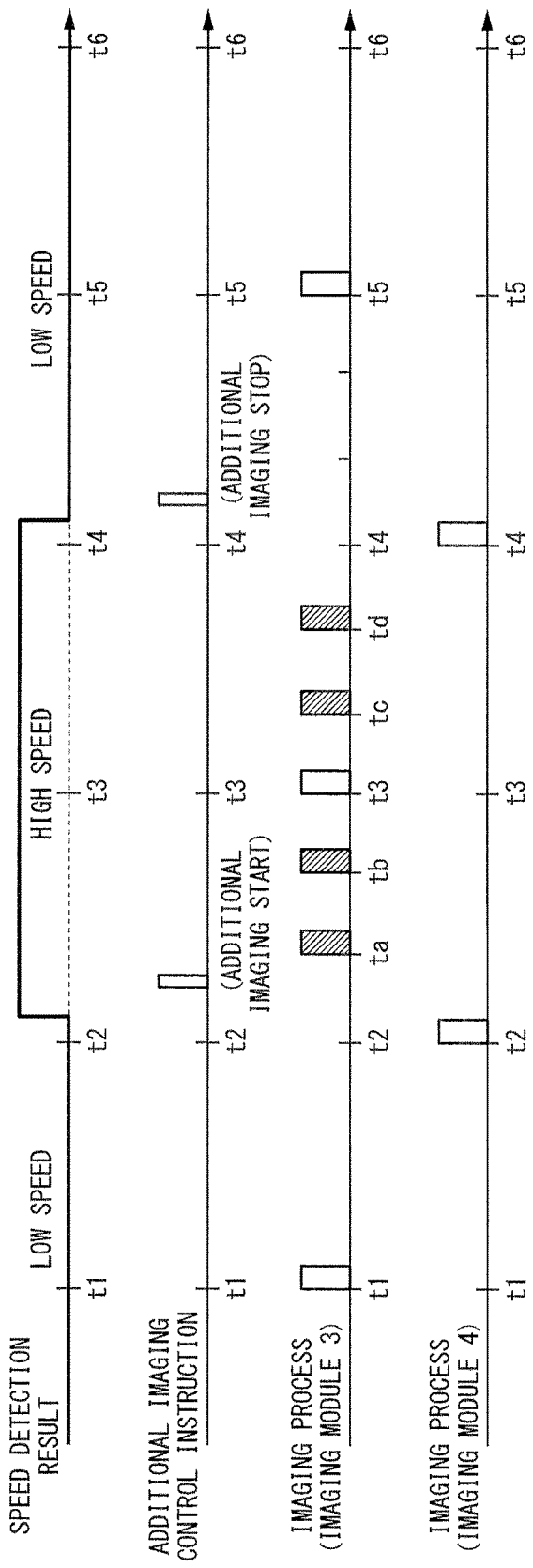
FIG. 13 is a timing chart illustrating timings of processing performed by the capsule endoscope in the second embodiment of the present invention.

FIG. 13 illustrates timings of various types of processing performed by the capsule endoscope 20 when the capsule endoscope 20 moves at the moving speed illustrated in FIG. 12. FIG. 13 illustrates a process performed by the capsule endoscope 20 at each time point illustrated in FIG. 12 using the passage of time as a reference (horizontal axis).

A procedure of executing the additional imaging will be described using FIG. 13. In FIG. 13, a result of detecting the moving speed of the capsule endoscope 20, timings at which a start instruction of the additional imaging and an end instruction of the additional imaging are performed, and timings of imaging processes by the imaging modules 3 and 4 of the capsule endoscope 20 are illustrated.

The imaging modules 3 and 4 alternately perform the imaging processes as described above. In FIG. 13, the imaging module 4 images the imaging range of the moving direction. In addition, in FIG. 13, the first time interval at which the imaging module 4 performs imaging is the same as the second time interval at which the imaging module 3 performs imaging.

In this embodiment, the capsule endoscope 20 moves at the high speed immediately after the imaging module 4 images the imaging range of the moving direction at the timing t2 and then the high-speed movement continues until a time immediately after the timing t4 at which the imaging range of the moving direction is imaged. Unlike the first embodiment, the change of the moving speed is detected substantially in real time because the moving speed is detected based on the acceleration detected by the acceleration sensor 22.

Thus, the additional imaging starts immediately after high-speed movement starts and the additional imaging by the imaging module 3 performing imaging in the backward direction starts at a timing ta. Thereafter, the additional imaging is executed periodically at a third time interval shorter than a second time interval at which normal imaging is performed (timings tb, tc, and td). As in the first embodiment, the additional imaging is executed at the timing at which the additional imaging does not overlap the normal imaging, that is, in a free time of the normal imaging. As illustrated in FIG. 13, the additional imaging is stopped even when the capsule endoscope 20 is moving at the high speed in the vicinity of the timing t4 at which the normal imaging is executed.

As the system derived in this embodiment, a system to which the following algorithm, which focuses on reduction of power consumption, is applied is considered. For example, there is an algorithm of stopping an imaging process related to the additional imaging scheduled at a timing close to a timing at which imaging of an imaging range of the backward direction is executed as normal imaging. In this case, in FIG. 13, the additional imaging of the timings tb and tc close to the timing of the normal imaging process to be performed at the timing t3 is stopped and the additional imaging is performed at the timings to and td.

In addition, there is an algorithm of executing the additional imaging only in a period in which the imaging directions of the normal imaging process do not face each other as another algorithm. In this case, because the imaging of the imaging range of the backward direction is performed at the timing t3 and the imaging of the imaging range of the moving direction is performed at the timing t4 in FIG. 13, the imaging directions of the timings t3 and t4 do not face each other. In this case, a region between a position at the timing t3 and a position at the timing t4 is not imaged. Thus, the additional imaging is performed at the timings tc and td.

In this embodiment, the image processing section 9, the image accumulating section 10, and the reception apparatus control section 14 are not essential components for obtaining a characteristic effect of the capsule endoscope system according to this embodiment. In addition, the moving direction and the moving speed of the capsule endoscope 20 may be detected using a configuration other than the acceleration sensor 22. Accordingly, the acceleration sensor 22 is not an essential component for obtaining a characteristic effect of the capsule endoscope system according to this embodiment.

According to this embodiment, a capsule endoscope system is configured to include: a capsule endoscope 20 having a first imaging module (imaging module 3 or 4) configured to direct an imaging direction in a first direction, image a first imaging range, and output first image data; a second imaging module (imaging module 3 or 4) configured to direct an imaging direction in a second direction different from the first direction, image a second imaging range that does not overlap the first imaging range, and output second image data; and a first wireless communication interface (transceiver 5) configured to transmit the first image data and the second image data; and a reception apparatus 2 having a second wireless communication interface (transceiver 8) configured to receive the first image data and the second image data, wherein the capsule endoscope 20 has a moving direction detecting section (capsule control section 21) configured to detect a moving direction of the capsule endoscope 20; a moving speed detecting section (capsule control section 21) configured to detect a moving speed of the capsule endoscope 20; a speed determining section (capsule control section 21) configured to determine whether the moving speed is greater than or equal to a predetermined speed; and an imaging instruction section (capsule control section 21) configured to instruct an imaging module having an imaging direction closer to a moving direction between the first and second imaging modules to perform imaging at a first time interval and instruct an imaging module having an imaging direction farther from the moving direction to perform imaging at a second time interval which is the same as or different from the first time interval when the moving speed is less than the predetermined speed, and perform additional imaging at a third time interval shorter than the second time interval if the imaging at the second time interval is in execution when the moving speed is greater than or equal to the predetermined speed.

In addition, according to this embodiment, the capsule endoscope 20 is configured to include: a first imaging module (imaging module 3 or 4) configured to direct an imaging direction in a first direction, image a first imaging range, and output first image data; a second imaging module (imaging module 3 or 4) configured to direct an imaging direction in a second direction different from the first direction, image a second imaging range that does not overlap the first imaging range, and output second image data; a wireless communication interface (transceiver 5) configured to transmit the first image data and the second image data; a moving direction detecting section (capsule control section 21) configured to detect a moving direction of the capsule endoscope 20; a moving speed detecting section (capsule control section 21) configured to detect a moving speed of the capsule endoscope 20; a speed determining section (capsule control section 21) configured to determine whether the moving speed is greater than or equal to a predetermined speed; and an imaging instruction section (capsule control section 21) configured to instruct an imaging module having an imaging direction closer to a moving direction between the first and second imaging modules to perform imaging at a first time interval and instruct an imaging module having an imaging direction farther from the moving direction to perform imaging at a second time interval which is the same as or different from the first time interval when the moving speed is less than the predetermined speed and perform additional imaging at a third time interval shorter than the second time interval if the imaging at the second time interval is in execution when the moving speed is greater than or equal to the predetermined speed.

In addition, according to this embodiment, an imaging control method of a capsule endoscope includes the step S13 of determining whether a moving speed of the capsule endoscope 20 is greater than or equal to a predetermined speed and the step S17 of instructing an imaging module having an imaging direction closer to a moving direction between the first imaging module (imaging module 3 or 4)

and the second imaging module (imaging module 3 or 4) to perform imaging at a first time interval and instructing an imaging module having an imaging direction farther from the moving direction to perform imaging at a second time interval which is the same as or different from the first time interval when the moving speed is less than the predetermined speed and perform additional imaging at a third time interval shorter than the second time interval if the imaging at the second time interval is in execution when the moving speed is greater than or equal to the predetermined speed.

In addition, according to this embodiment, a program is configured to cause a computer of the capsule endoscope 20 to execute: the step S13 of determining whether a moving speed of the capsule endoscope 20 is greater than or equal to a predetermined speed and the step S17 of instructing an imaging module having an imaging direction closer to a moving direction between the first imaging module (imaging module 3 or 4) and the second imaging module (imaging module 3 or 4) to perform imaging at a first time interval and instructing an imaging module having an imaging direction farther from the moving direction to perform imaging at a second time interval which is the same as or different from the first time interval when the moving speed is less than the predetermined speed and perform additional imaging at a third time interval shorter than the second time interval if the imaging at the second time interval is in execution when the moving speed is greater than or equal to the predetermined speed.

In this embodiment, it is possible to reduce discontinuity in imaging of a part of an imaging target occurring in association with instantaneous high-speed movement of the capsule endoscope by instructing the imaging module having the imaging direction farther from the moving direction to perform additional imaging at the third time interval shorter than the second time interval if the imaging at the second time interval is in execution when the moving speed is greater than or equal to the predetermined speed.

Using the configuration of the capsule endoscope system according to this embodiment, as in the first embodiment, only the imaging range of the moving direction may be imaged in normal imaging during low-speed movement and the imaging range of the backward direction may be imaged in additional imaging during high-speed movement. That is, the capsule control section 21 of this embodiment may instruct an imaging module having an imaging direction closer to a moving direction between the first and second imaging modules to perform imaging at a first time interval and instruct an imaging module having an imaging direction farther from the moving direction to stop imaging when the moving speed is less than the predetermined speed and perform additional imaging if the imaging is stopped when the moving speed is greater than or equal to the predetermined speed.

In addition, using the configuration of the capsule endoscope system according to the first embodiment, as in the second embodiment, the imaging range of the moving direction and the imaging range of the backward direction may be alternately imaged in normal imaging during low-speed movement and the imaging range of the backward direction may be imaged at a shorter time interval in additional imaging during high-speed movement. That is, the reception apparatus control section 14 of the first embodiment may instruct an imaging module having an imaging direction closer to a moving direction between the first and second imaging modules to perform imaging at a first time interval and instruct an imaging module having an imaging direction farther from the moving direction to perform imaging at a second time interval which is the same as or different from the first time interval when the moving speed is less than the predetermined speed and perform additional imaging at a third time interval shorter than the second time interval if the imaging at the second time interval is in execution when the moving speed is greater than or equal to the predetermined speed.

Third Embodiment

Next, the third embodiment of the present invention will be described. This embodiment is an example in which a capsule endoscope performs the detection of the moving direction and the moving speed of the capsule endoscope performed by a reception apparatus in the first embodiment.

Figure 14:
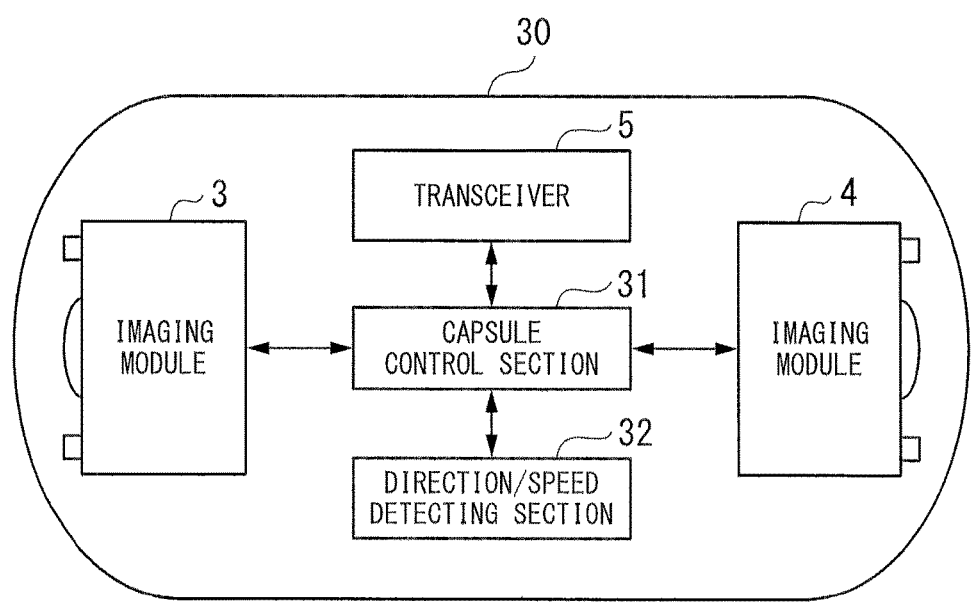
FIG. 14 is a block diagram illustrating a configuration example of a capsule endoscope according to a third embodiment of the present invention.

FIG. 14 illustrates a configuration example of the capsule endoscope 30 according to this embodiment. As illustrated in FIG. 14, the capsule endoscope 30 has an imaging module 3, an imaging module 4, a transceiver 5, a capsule control section 31, and a direction/speed detecting section 32. In the capsule endoscope 30 of this embodiment, the capsule control section 21 in the capsule endoscope 20 illustrated in FIG. 9 is changed to the capsule control section 31 and the direction/speed detecting section 32 configured to detect the moving direction and the moving speed of the capsule endoscope 30 from the image data is added in place of the acceleration sensor 22.

Direction data indicating the moving direction and speed data indicating the moving speed output from the direction/speed detecting section 32 are input to the capsule control section 31. The capsule control section 31 selects the imaging module that images the imaging range of the moving direction using the direction data and makes a determination related to execution of additional imaging using the speed data. According to a result of the determination related to the execution of the additional imaging, the capsule control section 31 controls the imaging modules 3 and 4 to perform the additional imaging.

A method in which the direction/speed detecting section 32 detects the moving direction and the moving speed of the capsule endoscope 30 from the image data is similar to the method in which the direction/speed detecting section 12 of the first embodiment detects the moving direction and the moving speed of the capsule endoscope 1 from the image data. In addition, because a process in which the capsule control section 31 makes the determination related to the additional imaging is similar to the process performed by the reception apparatus control section 14 of the first embodiment, description thereof will be omitted.

In relation to the driving of the imaging modules 3 and 4 in the normal imaging, either of the method of driving only the imaging module configured to image the imaging range of the moving direction shown in the first embodiment and the method of alternately driving the imaging module configured to image the imaging range of the moving direction and the imaging module configured to image the imaging range of the backward direction shown in the second embodiment can be adopted.

In this embodiment, as in the first and second embodiments, it is possible to reduce discontinuity in imaging of a part of an imaging target occurring in association with instantaneous high-speed movement of a capsule endoscope.

Fourth Embodiment

Next, the fourth embodiment of the present invention will be described. A capsule endoscope system according to this embodiment is a capsule endoscope system reducing discontinuity in imaging occurring when a capsule endoscope is temporarily in a still state (or a very low-speed state) immediately after the capsule endoscope moves at high speed and then starts low-speed movement.

First, the discontinuity in the imaging occurring when the moving speed of the capsule endoscope changes as described above will be described using FIG. 15. In the capsule endoscope system according to this embodiment, as in the first embodiment, the capsule endoscope normally images only the imaging range of the moving direction and the reception apparatus performs the detection of the moving speed and the instruction of the additional imaging. Hereinafter, description will be given using the configuration of the capsule endoscope system according to the first embodiment.

Figure 15:
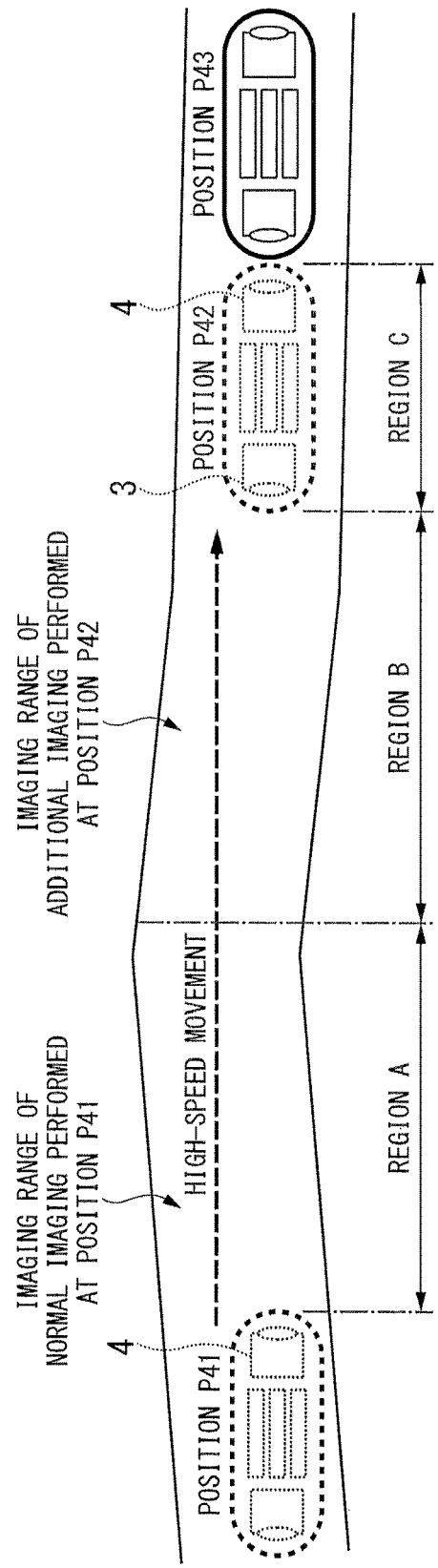
FIG. 15 is a reference diagram illustrating a position of a capsule endoscope in a fourth embodiment of the present invention.

FIG. 15 illustrates the position of the capsule endoscope 1 when the moving speed of the capsule endoscope 1 changes as described above. As illustrated in FIG. 15, the capsule endoscope 1 in this example moves from a position P41 to a position P42 at a high speed, then temporarily stops at the position P42, and then moves to a position P43 at a low speed. In this case, the imaging module 4 images a region A through normal imaging at the position P41 before the capsule endoscope 1 moves at the high speed and the imaging module 3 images a region B through additional imaging at the position P42 immediately after the capsule endoscope 1 moves at the high speed.

Because the capsule endoscope 1 stops at the position P42, only the region B is imaged through additional imaging and the additional imaging ends. Thereafter, when the capsule endoscope 1 moves at the low speed, imaging by the imaging module 4 starts from the position P42. Thus, the discontinuity in the imaging occurs in a region C between the imaging modules 3 and 4.

In order to prevent the discontinuity in the imaging from occurring in this embodiment, the capsule endoscope 1 continues the additional imaging at a relatively long time interval until a part of image data obtained by imaging of the imaging range of the moving direction is shown in image data obtained by the additional imaging of the imaging range of the backward direction without ending the additional imaging immediately after the high-speed movement ends.

The reception apparatus control section 14 of this embodiment instructs the imaging module having the imaging direction farther from the moving direction to stop the imaging when the moving speed is less than the predetermined speed and perform the additional imaging when the moving speed is greater than or equal to the predetermined speed. In addition, the reception apparatus control section 14 of this embodiment compares latest image data obtained from the imaging module having the imaging direction closer to the moving direction to latest image data obtained from the imaging module having the imaging direction farther from the moving direction when the moving speed is less than the predetermined speed after being greater than or equal to the predetermined speed, instructs the imaging module having the imaging direction farther from the moving direction to perform the additional imaging when the same part is not viewed between the image data of the two, and instructs the imaging module having the imaging direction farther from the moving direction to stop the imaging when the same part is viewed between the image data of the two.

Figure 16:
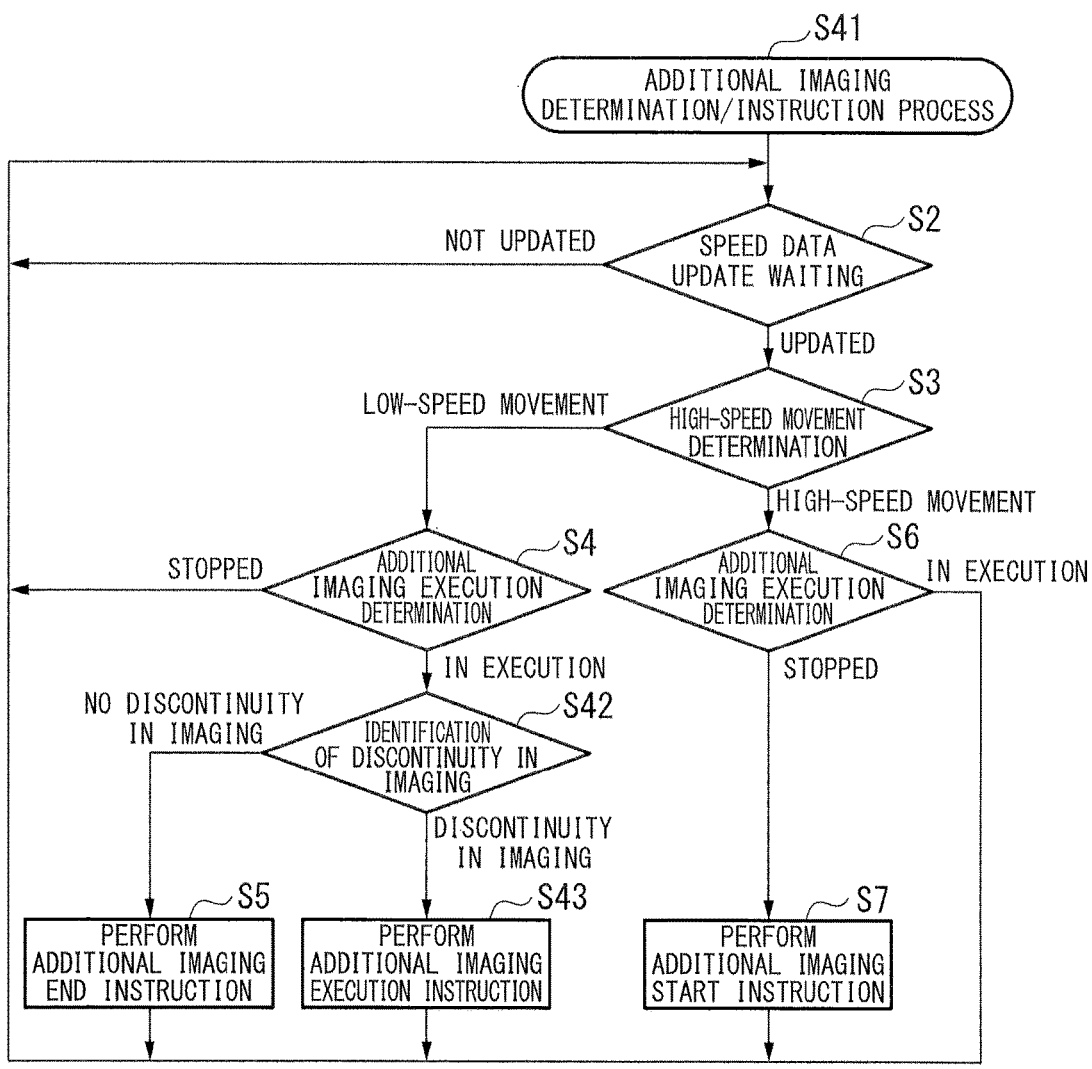
FIG. 16 is a flowchart illustrating a procedure of an additional imaging determination/instruction process performed by a reception apparatus according to the fourth embodiment of the present invention.

FIG. 16 illustrates a procedure of an additional imaging determination/instruction process S41 performed by the reception apparatus 2. In FIG. 16, the same processes as the processes illustrated in FIG. 4 in this first embodiment are assigned the same reference signs.

A difference between the additional imaging determination/instruction process S41 of this embodiment and the additional imaging determination/instruction process S1 of the first embodiment is that a process S42 to be performed when the movement of the capsule endoscope 1 changes from the high-speed movement to the low-speed movement and a process S43 of imaging a range in which the discontinuity in the imaging occurs are added. After the capsule endoscope 1 moves at the high speed, a determination S4 of whether the additional imaging is in execution is made when it is determined that the capsule endoscope 1 is moving at the low speed (S3). When it is determined that the additional imaging is in execution, the reception apparatus control section 14 performs identification S42 of discontinuity in imaging.

The identification S42 of the discontinuity in the imaging is a process of identifying whether a part of the image data obtained by imaging of the imaging range of the moving direction is provided in the image data obtained by the additional imaging of the imaging range of the backward direction. Specifically, the moving speed is less than the predetermined speed, and the reception apparatus control section 14 compares the latest image data obtained by the imaging of the imaging range of the moving direction immediately after the capsule endoscope 1 starts low-speed movement to the latest image data obtained by the additional imaging of the imaging range of the backward direction. Further, the reception apparatus control section 14 identifies whether the same part is between the image data of the two. If the same part is not found, it is determined that there is discontinuity in the imaging. If the same part is found, it is determined that there is no discontinuity in the imaging. Because this process can be performed by pattern detection that is general image processing, details of the process will not be described here.

While the capsule endoscope 1 moves from the position P42 of FIG. 15 to the position P43 in this embodiment, it is determined that there is discontinuity in the imaging and an additional imaging execution instruction S43 is executed. In the additional imaging execution instruction S43, the reception apparatus control section 14 instructs the imaging module having the imaging direction farther from the moving direction to perform additional imaging so that the imaging interval is a relatively long imaging interval (for example, a time interval greater than or equal to a first time interval at which normal imaging is performed).

After the capsule endoscope 1 moves to the position P43, it is determined that there is no discontinuity of the imaging in the identification S42 of the discontinuity in the imaging and an additional imaging end instruction S5 for instructing the imaging module having the imaging direction farther from the moving direction to end the additional imaging is executed. Through the above-described procedure, a region C of FIG. 15 is imaged by the additional imaging and the discontinuity in the imaging is eliminated.

In this embodiment, it is possible to perform the additional imaging of a region between two imaging modules immediately after the capsule endoscope 1 ends high-speed movement. Accordingly, it is possible to reduce discontinuity in imaging of a part of an imaging target occurring in association with instantaneous high-speed movement of the capsule endoscope.

Fifth Embodiment

Next, the fifth embodiment of the present invention will be described. As in the fourth embodiment, the capsule endoscope system according to this embodiment is a capsule endoscope system reducing discontinuity in imaging occurring when the capsule endoscope is temporarily in a still state (or a very low-speed state) immediately after the capsule endoscope moves at a high speed and then starts low-speed movement. Hereinafter, description will be given using the configuration of the capsule endoscope system according to the second embodiment.

A difference from the fourth embodiment is that the determination of whether there is discontinuity in imaging is made based on a movement distance obtained from acceleration data without comparing image data. Specifically, a process in which the capsule endoscope 20 further moves to a position P43 after moving to a position P42 of FIG. 15 is detected based on the movement distance calculated from acceleration data. The imaging of a region C is performed by executing additional imaging at a point in time at which it is determined that the capsule endoscope 20 reaches the position P43.

In this embodiment, the case in which the capsule endoscope 20 having the built-in acceleration sensor 22 illustrated in FIG. 9 normally images only the imaging range of the moving direction as in the first embodiment and the capsule endoscope 20 makes the determination related to the execution of the additional imaging will be described as an example.

The capsule control section 21 of this embodiment instructs the imaging module having the imaging direction farther from the moving direction to stop the imaging when the moving speed is less than the predetermined speed and perform the additional imaging when the moving speed is greater than or equal to the predetermined speed. In addition, when the moving speed is less than the predetermined speed after being greater than or equal to the predetermined speed, the capsule control section 21 of this embodiment instructs the imaging module having the imaging direction farther from the moving direction to execute the additional imaging at a point in time at which it is estimated that the capsule endoscope 20 is moved by a distance corresponding to a total length (capsule length) of the capsule endoscope 20 or greater than or equal to a length of a range between the imaging module 3 and the imaging module 4 from the position of the capsule endoscope 20 of a point in time at which the additional imaging has been finally performed.

Figure 17:
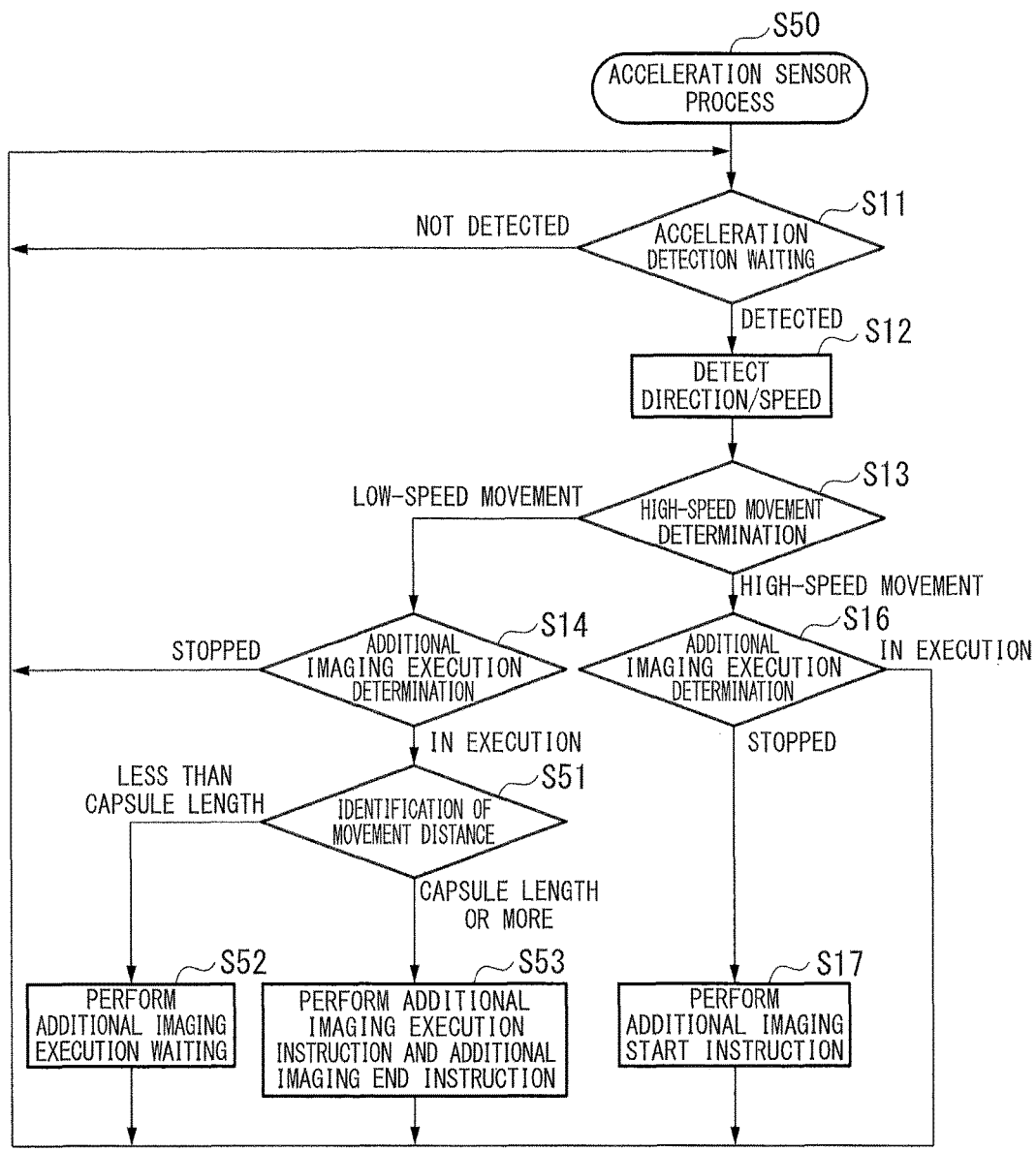
FIG. 17 is a flowchart illustrating a procedure of an acceleration sensor process performed by a capsule endoscope according to a fifth embodiment of the present invention.

FIG. 17 illustrates a procedure of an acceleration sensor process S50 that is a process to be performed by the capsule control section 21 based on the acceleration data from the acceleration sensor 22. In FIG. 17, the same processes as processes illustrated in FIG. 10 in the second embodiment are assigned the same reference signs.

A difference between the acceleration sensor process S50 of this embodiment and the acceleration sensor process S10 of the second embodiment is that identification S51 of the movement distance, additional imaging execution waiting S52, and an additional imaging execution instruction and additional imaging end instruction S53 are executed. The identification S51 of the movement distance is a process to be performed when the movement of the capsule endoscope 20 changes from the high-speed movement to the low-speed movement. The additional imaging execution waiting S52 is a process of waiting for the movement to the position P43 of FIG. 15 by the capsule endoscope 20 to be completed. The additional imaging execution instruction and additional imaging end instruction S53 are a process of imaging a range in which the discontinuity in the imaging occurs according to additional imaging after the capsule endoscope 20 completes the movement to the position P43 of FIG. 15.

When it is determined that the capsule endoscope 20 is moving at the low speed (S13) after the capsule endoscope 20 moves at the high speed, a determination S14 of whether the additional imaging is in execution is made. When it is determined that the additional imaging is in execution, the capsule control section 21 performs the identification S51 of the movement distance. In the identification S51 of the movement distance, the capsule control section 21 estimates the movement distance of the capsule endoscope 20 from a point in time at which the additional imaging has been finally performed after the capsule endoscope 20 has started the low-speed movement based on acceleration data output from the acceleration sensor 22. Further, in the identification S51 of the movement distance, the capsule control section 21 determines whether the movement distance is longer than the total length of the capsule endoscope 20. Although the total length of the capsule endoscope 20 is a threshold value of the determination in the identification S51 of the movement distance in the present description, a length of the range between the imaging modules 3 and 4 may be the threshold value.

When it is determined that the movement distance is shorter than the total length of the capsule endoscope 20, the additional imaging execution waiting S52 is executed and the capsule endoscope 20 is in a state of waiting for execution of the additional imaging. At a point in time at which it is determined that the movement distance is greater than or equal to the total length of the capsule endoscope 20, the additional imaging execution instruction and additional imaging end instruction S53 are executed. This time point is a point in time at which it is estimated that the capsule endoscope 20 is moved by a distance greater than or equal to the total length (capsule length) of the capsule endoscope 20 from the position of the capsule endoscope 20 of the point in time at which the additional imaging has been finally performed.

In the additional imaging execution instruction and additional imaging end instruction S53, the capsule control section 21 instructs the imaging module having the imaging direction farther from the moving direction to execute the additional imaging. As described above, the capsule control section 21 stores information indicating the imaging module having the imaging direction farther from the moving direction, that is, the imaging module that performs the additional imaging. The capsule control section 21 instructs the imaging module indicated by the information to execute the additional imaging. Immediately after the additional imaging is executed, the capsule control section 21 instructs the module having the imaging direction farther from the moving direction to end the additional imaging.

In this embodiment, it is possible to perform additional imaging of a region between two imaging modules immediately after the capsule endoscope 20 ends high-speed movement. Accordingly, it is possible to reduce discontinuity in imaging of a part of an imaging target occurring in association with instantaneous high-speed movement of the capsule endoscope.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A capsule endoscope system comprising:
a capsule endoscope having
a first imaging module configured to capture an image in a first direction, image a first imaging area, and output first image data,
a second imaging module configured to capture an image in a second direction different from the first direction, image a second imaging area that does not overlap the first imaging area, and output second image data, and
a first wireless communication interface configured to transmit the first image data and the second image data; and
a receiver having a second wireless communication interface configured to receive the first image data and the second image data,
wherein the capsule endoscope or the receiver has
a processor configured:
to detect a moving direction of the capsule endoscope,
to detect a moving speed of the capsule endoscope, and
to determine whether the moving speed is greater than or equal to a predetermined speed, and
a device controller configured to instruct an imaging module selected from the first and second imaging modules whose imaging direction is closer to a moving direction begin imaging at a first time interval,
to instruct the other imaging module, which is farther from the moving direction, to stop imaging or to begin imaging at a second time interval which is the same as or different from the first time interval when the moving speed is less than the predetermined speed, and
to instruct the farther imaging module to begin additional imaging if the imaging is stopped and to begin additional imaging at a third time interval shorter than the second time interval if the imaging at the second time interval is in execution when the moving speed is greater than or equal to the predetermined speed.

2. The capsule endoscope system according to claim 1,
wherein the processor detects a moving direction of the capsule endoscope from the first image data or the second image data, and
wherein the processor detects a moving speed of the capsule endoscope from the first image data or the second image data.

3. The capsule endoscope system according to claim 2,
wherein the receiver includes the processor, and
wherein the device controller transmits instruction data indicating an instruction of any one of imaging at the first time interval, stop of the imaging, imaging at the second time interval, additional imaging, and additional imaging at the third time interval shorter than the second time interval from the second wireless communication interface to the capsule endoscope.

4. The capsule endoscope system according to claim 2, wherein the capsule endoscope includes the processor.

5. The capsule endoscope system according to claim 4,
wherein the capsule endoscope further has an acceleration sensor configured to detect acceleration of the capsule endoscope,
wherein the processor detects the moving direction based on the acceleration of the capsule endoscope detected by the acceleration sensor, and
wherein the processor detects the moving speed based on the acceleration of the capsule endoscope detected by the acceleration sensor.

6. The capsule endoscope system according to claim 3,
wherein the device controller instructs the imaging module having the imaging direction farther from the moving direction to stop the imaging when the moving speed is less than the predetermined speed and perform the additional imaging when the moving speed is greater than or equal to the predetermined speed, and
wherein the device controller compares latest image data obtained from the imaging module having the imaging direction closer to the moving direction to latest image data obtained from the imaging module having the imaging direction farther from the moving direction when the moving speed is less than the predetermined speed after being greater than or equal to the predetermined speed and instructs the imaging module having the imaging direction farther from the moving direction to perform the additional imaging when the same part is not viewed between the image data of the two and stop the imaging when the same part is viewed between the image data of the two.

7. The capsule endoscope system according to claim 5,
wherein the device controller instructs the imaging module having the imaging direction farther from the moving direction to stop the imaging when the moving speed is less than the predetermined speed and perform the additional imaging when the moving speed is greater than or equal to the predetermined speed, and
wherein the device controller instructs the imaging module having the imaging direction farther from the moving direction to perform the additional imaging at a point in time at which it is estimated that the capsule endoscope is moved by a distance corresponding to a total length of the capsule endoscope or greater than or equal to a length of a range between the first imaging module and the second imaging module from a position of the capsule endoscope of a point in time at which the additional imaging has been finally performed when the moving speed is less than the predetermined speed after being greater than or equal to the predetermined speed.

8. A receiver comprising:
a wireless communication interface configured to receive first image data and second image data from a capsule endoscope having a first imaging module configured to capture an image in a first direction, image a first imaging area, and output the first image data; a second imaging module configured to capture an image in a second direction different from the first direction, image a second imaging range that does not overlap the first imaging area, and output the second image data; and a first wireless communication interface configured to transmit the first image data and the second image data;
a processor configured to detect a moving direction of the capsule endoscope;
to detect a moving speed of the capsule endoscope;
to determine whether the moving speed is greater than or equal to a predetermined speed; and
a device controller configured:
to transmit instruction data for instructing an imaging module selected from the first and second imaging modules whose imaging direction is closer to a moving direction to begin imaging at a first time interval,
and to instruct the other imaging module farther from the moving direction to stop imaging or to begin imaging at a second time interval which is the same as or different from the first time, and to instruct the farther imaging module to begin additional imaging if the imaging is stopped and to begin additional imaging at a third time interval shorter than the second time interval if the imaging at the second time interval is in execution when the moving speed is greater than or equal to the predetermined speed from the second wireless communication interface to the capsule endoscope.

\* \* \* \* \*